US011331029B2

(12) United States Patent
Schwartz et al.

(10) Patent No.: US 11,331,029 B2
(45) Date of Patent: May 17, 2022

(54) ESOPHAGUS POSITION DETECTION BY ELECTRICAL MAPPING

(71) Applicant: Navix International Limited, Road Town (VG)

(72) Inventors: Yitzhack Schwartz, Haifa (IL); Zalman Ibragimov, Rehovot (IL); Yehonatan Ben David, Tel-Aviv (IL); Yizhaq Shmayahu, Ramat-HaSharon (IL); Eli Dichterman, Haifa (IL); Shlomo Ben-Haim, Milan (IT)

(73) Assignee: Navix International Limited, Road Town (VG)

( * ) Notice: Subject to any disclaimer, the term of this patent is extended or adjusted under 35 U.S.C. 154(b) by 343 days.

(21) Appl. No.: 16/461,010

(22) PCT Filed: Nov. 16, 2017

(86) PCT No.: PCT/IB2017/057185
§ 371 (c)(1),
(2) Date: May 15, 2019

(87) PCT Pub. No.: WO2018/092070
PCT Pub. Date: May 24, 2018

(65) Prior Publication Data
US 2020/0163569 A1    May 28, 2020

Related U.S. Application Data

(60) Provisional application No. 62/546,775, filed on Aug. 17, 2017, provisional application No. 62/445,433,
(Continued)

(51) Int. Cl.
*A61B 5/285* (2021.01)
*A61B 5/0538* (2021.01)
(Continued)

(52) U.S. Cl.
CPC ............ *A61B 5/285* (2021.01); *A61B 5/0538* (2013.01); *A61B 5/1076* (2013.01); *A61B 5/4233* (2013.01); *A61B 5/742* (2013.01)

(58) Field of Classification Search
CPC ..... A61B 5/285; A61B 5/0538; A61B 5/1076; A61B 5/4233; A61B 5/742; A61B 5/287;
(Continued)

(56) References Cited

U.S. PATENT DOCUMENTS

| 4,917,097 A | 4/1990 | Proudian et al. |
| 5,109,851 A * | 5/1992 | Jadvar .................... A61B 5/287 600/439 |

(Continued)

FOREIGN PATENT DOCUMENTS

| CA | 2237992 | 3/1998 |
| CN | 1853573 | 11/2006 |

(Continued)

OTHER PUBLICATIONS

International Preliminary Report on Patentability dated May 31, 2019 From the International Bureau of WIPO Re. Application No. PCT/IB2017/057185. (11 Pages).
(Continued)

*Primary Examiner* — Sean P Dougherty

(57) ABSTRACT

A method of estimating a spatial relationship between at least a part of a patient esophagus and a heart chamber, including: measuring at least one electric parameter at one or more positions within the heart chamber to obtain measured values; and estimating the spatial relationship based on the measured values.

26 Claims, 16 Drawing Sheets

Related U.S. Application Data filed on Jan. 12, 2017, provisional application No. 62/422,767, filed on Nov. 16, 2016.

(51) Int. Cl.
*A61B 5/107* (2006.01)
*A61B 5/00* (2006.01)

(58) Field of Classification Search
CPC ...... A61B 18/1492; A61B 2018/00577; A61B 2018/00351; A61B 2090/061; A61B 5/06; A61B 5/6852

See application file for complete search history.

(56) References Cited

U.S. PATENT DOCUMENTS

| | | | |
|---|---|---|---|
| 5,529,568 A | 6/1996 | Rayman | |
| 5,553,611 A | 9/1996 | Budd et al. | |
| 5,662,108 A | 9/1997 | Budd et al. | |
| 5,697,377 A | 12/1997 | Wittkampf | |
| 5,724,978 A | 3/1998 | Tenhoff | |
| 5,846,198 A * | 12/1998 | Killmann | A61B 5/282 600/424 |
| 5,983,126 A | 11/1999 | Wittkampf | |
| 6,019,725 A | 2/2000 | Vesely et al. | |
| 6,038,468 A | 3/2000 | Rex | |
| 6,240,307 B1 | 5/2001 | Beatty et al. | |
| 6,266,552 B1 | 7/2001 | Slettenmark | |
| 6,317,621 B1 | 11/2001 | Graumann et al. | |
| 6,322,558 B1 | 11/2001 | Taylor et al. | |
| 6,423,057 B1 | 7/2002 | He et al. | |
| 6,515,657 B1 | 2/2003 | Zanelli | |
| 6,640,119 B1 | 10/2003 | Budd et al. | |
| 6,728,562 B1 | 4/2004 | Budd et al. | |
| 6,826,420 B1 | 11/2004 | Beatty et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,187,973 B2 | 3/2007 | Hauck | |
| 7,189,208 B1 | 3/2007 | Beatty et al. | |
| 7,881,769 B2 | 2/2011 | Sobe | |
| 7,996,060 B2 | 8/2011 | Trofimov et al. | |
| 8,355,801 B2 † | 1/2013 | O'Sullivan | |
| 2002/0068931 A1 | 6/2002 | Wong et al. | |
| 2003/0074011 A1 | 4/2003 | Gilboa et al. | |
| 2003/0220636 A1 | 11/2003 | Bowman et al. | |
| 2004/0039278 A1 | 2/2004 | Wacker et al. | |
| 2004/0044279 A1 | 3/2004 | Lewin et al. | |
| 2004/0097805 A1 | 5/2004 | Verard et al. | |
| 2004/0147920 A1 | 7/2004 | Keidar | |
| 2004/0176804 A1 | 9/2004 | Palti | |
| 2005/0015006 A1 | 1/2005 | Mitschke et al. | |
| 2005/0033164 A1 | 2/2005 | Yatsuo et al. | |
| 2005/0054913 A1 | 3/2005 | Duerk et al. | |
| 2005/0054918 A1 | 3/2005 | Sra | |
| 2005/0058328 A1 | 3/2005 | Moreau-Gobard | |
| 2005/0245814 A1 | 11/2005 | Anderson et al. | |
| 2006/0089552 A1 | 4/2006 | Goldbach | |
| 2006/0241401 A1 | 10/2006 | Govari et al. | |
| 2006/0287604 A1 * | 12/2006 | Hickey | A61B 5/02158 600/508 |
| 2007/0043296 A1 | 2/2007 | Schwartz | |
| 2007/0049915 A1 | 3/2007 | Haemmerich et al. | |
| 2007/0106287 A1 | 5/2007 | O'Sullivan | |
| 2007/0106289 A1 | 5/2007 | O'Sullivan | |
| 2007/0167706 A1 | 7/2007 | Boese et al. | |
| 2007/0167726 A1 | 7/2007 | Unal et al. | |
| 2008/0114235 A1 | 5/2008 | Unal et al. | |
| 2008/0118135 A1 | 5/2008 | Averbuch et al. | |
| 2008/0125775 A1 | 5/2008 | Morris | |
| 2008/0177175 A1 | 7/2008 | Mottola et al. | |
| 2008/0183070 A1 | 7/2008 | Unai et al. | |
| 2008/0190438 A1 | 8/2008 | Harlev et al. | |
| 2008/0208031 A1 | 8/2008 | Kurpad et al. | |
| 2008/0221425 A1 | 9/2008 | Olson et al. | |
| 2008/0275440 A1 | 11/2008 | Kratoska et al. | |
| 2008/0275465 A1 | 11/2008 | Paul et al. | |
| 2009/0010519 A1 | 1/2009 | Wakai et al. | |
| 2009/0015818 A1 | 1/2009 | Ikeda et al. | |
| 2009/0062684 A1 * | 3/2009 | Gregersen | A61B 5/4233 600/547 |
| 2009/0148012 A1 | 6/2009 | Altmann et al. | |
| 2009/0171274 A1 | 7/2009 | Harlev et al. | |
| 2009/0221908 A1 | 9/2009 | Glossop | |
| 2009/0225077 A1 | 9/2009 | Sudarsky et al. | |
| 2009/0262109 A1 | 10/2009 | Markowitz et al. | |
| 2009/0275828 A1 | 11/2009 | Shachar et al. | |
| 2009/0281566 A1 | 11/2009 | Edwards et al. | |
| 2009/0299424 A1 * | 12/2009 | Narayan | A61B 5/0036 607/9 |
| 2010/0063400 A1 | 3/2010 | Hall et al. | |
| 2010/0217116 A1 | 8/2010 | Eck et al. | |
| 2010/0249579 A1 | 9/2010 | Starks | |
| 2010/0274239 A1 | 10/2010 | Paul et al. | |
| 2010/0283484 A1 | 11/2010 | Cohen et al. | |
| 2010/0312094 A1 | 12/2010 | Guttman et al. | |
| 2011/0106221 A1 | 5/2011 | Neal, II et al. | |
| 2011/0230758 A1 | 9/2011 | Eichler | |
| 2011/0276046 A1 † | 11/2011 | Heimbecher | |
| 2011/0282186 A1 | 11/2011 | Harlev et al. | |
| 2012/0059249 A1 | 3/2012 | Verard et al. | |
| 2012/0078129 A1 | 3/2012 | Bailin | |
| 2012/0109115 A1 | 5/2012 | Condie et al. | |
| 2012/0123250 A1 | 5/2012 | Pang et al. | |
| 2012/0150046 A1 | 6/2012 | Watson et al. | |
| 2012/0172724 A1 | 7/2012 | Hill et al. | |
| 2012/0173217 A1 | 7/2012 | Heimbecher | |
| 2012/0197243 A1 | 8/2012 | Sherman et al. | |
| 2012/0238866 A1 | 9/2012 | Wang et al. | |
| 2013/0137980 A1 | 5/2013 | Waters et al. | |
| 2013/0272593 A1 | 10/2013 | Lee et al. | |
| 2013/0310673 A1 | 11/2013 | Govari et al. | |
| 2014/0024911 A1 | 1/2014 | Harlev et al. | |
| 2014/0088943 A1 | 3/2014 | Trayanova et al. | |
| 2014/0187949 A1 | 7/2014 | Zhao et al. | |
| 2014/0243641 A1 | 8/2014 | Boveja et al. | |
| 2014/0243813 A1 | 8/2014 | Paul et al. | |
| 2014/0275991 A1 | 9/2014 | Potter et al. | |
| 2014/0330111 A1 | 11/2014 | Lichtenstein et al. | |
| 2015/0080762 A1 | 3/2015 | Kassab et al. | |
| 2015/0099942 A1 | 4/2015 | Edouard | |
| 2015/0173697 A1 * | 6/2015 | Parks | A61B 6/463 600/301 |
| 2015/0223757 A1 | 8/2015 | Werneth et al. | |
| 2015/0297099 A1 * | 10/2015 | Arad (Abboud) | A61B 5/0205 600/375 |
| 2016/0095651 A1 | 4/2016 | Deno et al. | |
| 2016/0095653 A1 | 4/2016 | Lambert et al. | |
| 2016/0242667 A1 | 8/2016 | Fay et al. | |
| 2016/0270683 A1 | 9/2016 | Grass et al. | |
| 2017/0014181 A1 | 1/2017 | Bar-Tal et al. | |
| 2017/0156792 A1 | 6/2017 | Ziv-Ari et al. | |
| 2017/0360369 A1 * | 12/2017 | Geist | A61B 5/4836 |
| 2018/0078195 A1 * | 3/2018 | Sutaria | A61B 5/065 |
| 2018/0153437 A1 | 6/2018 | Schwartz et al. | |
| 2019/0059782 A1 * | 2/2019 | Valderrabano | A61B 5/283 |
| 2019/0117103 A1 * | 4/2019 | Wildhaber | A61B 5/366 |
| 2021/0393327 A1 * | 12/2021 | Eyster | A61B 18/1492 |

FOREIGN PATENT DOCUMENTS

| | | |
|---|---|---|
| CN | 1915183 | 2/2007 |
| CN | 101327124 | 12/2008 |
| CN | 101676004 | 3/2010 |
| CN | 101912265 | 12/2010 |
| CN | 103327887 | 9/2013 |
| DE | 102006001884 | 7/2007 |
| EP | 0974936 | 1/2000 |
| EP | 1472975 | 11/2004 |
| EP | 1504713 | 2/2005 |
| EP | 1726268 | 11/2006 |
| EP | 1767166 | 3/2007 |

(56) References Cited

FOREIGN PATENT DOCUMENTS

| | | |
|---|---|---|
| EP | 1853162 | 11/2007 |
| EP | 1943974 | 7/2008 |
| EP | 2075763 | 7/2009 |
| EP | 2248480 | 11/2010 |
| EP | 2712543 | 4/2014 |
| EP | 2777584 | 9/2014 |
| ES | 2255230 | 6/2006 |
| HR | 20131208 | 3/2014 |
| JP | 2001-340336 | 12/2001 |
| WO | WO 97/29682 | 8/1997 |
| WO | WO 98/01069 | 1/1998 |
| WO | WO 2007/067628 | 6/2007 |
| WO | WO 2008/097767 | 8/2008 |
| WO | WO 2008/104914 | 9/2008 |
| WO | WO 2010/102794 | 9/2010 |
| WO | WO 2010/129095 | 11/2010 |
| WO | WO 2011/142931 | 11/2011 |
| WO | WO 2012/092016 | 7/2012 |
| WO | WO 2013/192598 | 12/2013 |
| WO | WO 2014/118535 | 8/2014 |
| WO | WO 2014/182822 | 11/2014 |
| WO | WO 2016/038499 | 3/2016 |
| WO | WO 2016/088084 | 6/2016 |
| WO | WO 2016/135584 | 9/2016 |
| WO | WO 2016/181315 | 11/2016 |
| WO | WO 2016/181316 | 11/2016 |
| WO | WO 2016/181317 | 11/2016 |
| WO | WO 2016/181318 | 11/2016 |
| WO | WO 2016/181320 | 11/2016 |
| WO | WO 2018/011757 | 1/2018 |
| WO | WO 2018/078540 | 5/2018 |
| WO | WO 2018/092059 | 5/2018 |
| WO | WO 2018/092062 | 5/2018 |
| WO | WO 2018/092063 | 5/2018 |
| WO | WO 2018/092070 | 5/2018 |
| WO | WO 2018/092071 | 5/2018 |
| WO | WO 2018/130974 | 7/2018 |
| WO | WO 2018/130976 | 7/2018 |
| WO | WO 2018/130981 | 7/2018 |
| WO | WO 2018/134747 | 7/2018 |
| WO | WO 2018/146613 | 8/2018 |
| WO | WO 2018/207128 | 11/2018 |
| WO | WO 2019/034944 | 2/2019 |
| WO | WO 2019/035023 | 2/2019 |
| WO | WO 2019/111180 | 6/2019 |

OTHER PUBLICATIONS

International Search Report and the Written Opinion dated Sep. 25, 2018 From the International Searching Authority Re. Application No. PCT/IB2018/050784. (18 Pages).
Invitation to Pay Additional Fees, Communication Relating to the Results of the Partial International Search and the Provisional Opinion dated Jun. 26, 2018 From the International Searching Authority Re. Application No. PCT/IB2018/050784. (13 Pages).
Boston Scientific "Rhythmia™ Mapping System: Rhythmia Dispossables Product Information: Intellamap Orion™ High Resolution Mapping Catheter", Boston Scientifc, 2 P., Sep. 2015.
International Search Report and the Written Opinion dated Jun. 7, 2018 From the International Searching Authority Re. Application No. PCT/IB2018/050289. (16 Pages).
Communication Relating to the Results of the Partial International Search dated Aug. 22, 2016 From the International Searching Authority Re. Application No. PCT/IB2016/052686.
Communication Relating to the Results of the Partial International Search dated Aug. 22, 2016 From the International Searching Authority Re. Application No. PCT/IB2016/052688.
Communication Relating to the Results of the Partial International Search dated Aug. 25, 2016 From the International Searching Authority Re. Application No. PCT/IB2016/052692.
Communication Relating to the Results of the Partial International Search dated Aug. 26, 2016 From the International Searching Authority Re. Application No. PCT/IB2016/052687.
International Preliminary Report on Patentability dated May 9, 2019 From the International Bureau of WIPO Re. Application No. PCT/IB2017/056616. (8 Pages).
International Preliminary Report on Patentability dated Nov. 23, 2017 From the International Bureau of WIPO Re. Application No. PCT/IB2016/052686. (11 Pages).
International Preliminary Report on Patentability dated Nov. 23, 2017 From the International Bureau of WIPO Re. Application No. PCT/IB2016/052687. (10 Pages).
International Preliminary Report on Patentability dated Nov. 23, 2017 From the International Bureau of WIPO Re. Application No. PCT/IB2016/052688. (9 Pages).
International Preliminary Report on Patentability dated Nov. 23, 2017 From the International Bureau of WIPO Re. Application No. PCT/IB2016/052690. (9 Pages).
International Preliminary Report on Patentability dated Nov. 23, 2017 From the International Bureau of WIPO Re. Application No. PCT/IB2016/052692. (13 Pages).
International Preliminary Report on Patentability dated May 31, 2019 From the International Bureau of WIPO Re. Application No. PCT/IB2017/057186. (13 Pages).
International Search Report and the Written Opinion dated Feb. 1, 2018 From the International Searching Authority Re. Application No. PCT/IB2017/056616. (14 Pages).
International Search Report and the Written Opinion dated Jan. 2, 2019 From the International Searching Authority Re. Application No. PCT/IB2018/056158. (16 Pages).
International Search Report and the Written Opinion dated Jan. 3, 2017 From the International Searching Authority Re. Application No. PCT/IB2016/052688. (14 Pages).
International Search Report and the Written Opinion dated May 3, 2018 From the International Searching Authority Re. Application No. PCT/IB2017/057185. (18 Pages).
International Search Report and the Written Opinion dated Jun. 6, 2018 From the International Searching Authority Re. Application No. PCT/IB2018/050201. (24 Pages).
International Search Report and the Written Opinion dated May 9, 2018 From the International Searching Authority Re. Application No. PCT/IB2018/050192. (16 Pages).
International Search Report and the Written Opinion dated Oct. 12, 2016 From the International Searching Authority Re. Application No. PCT/IB2016/052686.
International Search Report and the Written Opinion dated Aug. 13, 2018 From the International Searching Authority Re. Application No. PCT/IB2018/053258. (15 Pages).
International Search Report and the Written Opinion dated Apr. 14, 2019 From the International Searching Authority Re. Application No. PCT/IB2018/059672. (49 Pages).
International Search Report and the Written Opinion dated Oct. 16, 2017 From the International Searching Authority Re. Application No. PCT/IB2017/054263. (16 Pages).
International Search Report and the Written Opinion dated Oct. 17, 2016 From the International Searching Authority Re. Application No. PCT/IB2016/052692.
International Search Report and the Written Opinion dated Oct. 21, 2016 From the International Searching Authority Re. Application No. PCT/IB2016/052687. (16 Pages).
International Search Report and the Written Opinion dated Feb. 22, 2018 From the International Searching Authority Re. Application No. PCT/IB2017/057169. (14 Pages).
International Search Report and the Written Opinion dated Feb. 22, 2018 From the International Searching Authority Re. Application No. PCT/IB2017/057175. (15 Pages).
International Search Report and the Written Opinion dated Feb. 22, 2018 From the International Searching Authority Re. Application No. PCT/IB2017/057176. (15 Pages).
International Search Report and the Written Opinion dated Aug. 25, 2016 From the International Searching Authority Re. Application No. PCT/IB2016/052690.
International Search Report and the Written Opinion dated Apr. 30, 2018 From the International Searching Authority Re. Application No. PCT/IB2017/057186. (22 Pages).

(56) References Cited

OTHER PUBLICATIONS

International Search Report and the Written Opinion dated Apr. 30, 2018 From the International Searching Authority Re. Application No. PCT/IB2018/050195. (16 Pages).
International Search Report and the Written Opinion dated Nov. 30, 2018 From the International Searching Authority Re. Application No. PCT/IB2018/055344. (15 Pages).
Invitation to Pay Additional Fees and Communication Related to the Results of the Partial International Search and the Provisional Opinion dated Feb. 22, 2018 From the International Searching Authority Re. Application No. PCT/IB2017/057186. (12 Pages).
Invitation to Pay Additional Fees, Communication Relating to the Results of the Partial International Search and the Provisional Opinion dated Mar. 5, 2018 From the International Searching Authority Re. Application No. PCT/IB2017/057185. (13 Pages).
Invitation to Pay Additional Fees, Communication Relating to the Results of the Partial International Search and the Provisional Opinion dated Apr. 25, 2018 From the International Searching Authority Re. Application No. PCT/TB2018/050201. (14 Pages).
Notice of Allowance dated Dec. 26, 2018 From the US Patent and Trademark Office Re. U.S. Appl. No. 15/572,815. (8 pages).
Official Action dated Aug. 30, 2018 From the US Patent and Trademark Office Re. U.S. Appl. No. 15/572,815. (22 pages).
Ahn et al. "Height-Based Deformation and Ray Supersampling for Colon Unfolding", ICAT'06 Proceedings of the 16th International Conference on Advances in Artificial Reality and Tele-Existence, Lecture Notes in Computer Science, XP047402101, Hangzhou, China, Nov. 29-Dec. 1, 2006, p. 1098-1107, Nov. 29, 2006. Sections 3.1, 3.3, 5, Figs.2, 4, 5.
Anter et al. "Evaluation of a Novel High-Resolution Mapping Technology for Ablation of Recurrent Scar-Related Atrial Tachycardias," Heart Rhythm. 13(10): 2048-2055, Oct. 2016.
Arujuna et al. "Acute Pulmonary Vein Isolation Is Achieved by a Combination of Reversible and Irreversible Atrial Injury After Catheter Ablation: Evidence From Magnetic Resonance Imaging", Circulation: Arrhythmia and Electrophysiology, 5(4): 691-700, Published Online May 31, 2012.
Bartroli et al. "Nonlinear Virtual Colon Unfolding", Proceedings of the IEEE Conference on Visualization '01, VIS '01, XP031385694, San Diego, CA, USA, Oct. 21-26, 2001, p. 411-420, Oct. 21, 2001. Sections 4, 4.1, 4.2, 5.1, 7, Figs.1, 7a, 7b, 10.
Black-Maier et al. "Risk of Atrioesophageal Fistula Formation With Contact-Force Sensing Catheters", HeartRhythm, 14(9): 1328-1333, Published Online Apr. 15, 2017.
Bourier et al. "Electromagnetic Contact-Force Sensing Electrophysiological Catheters: How Accurate Is the Technology?", Journal of Cardiovascular Electrophysiology, 27(3): 347-350, Published Online Jan. 16, 2016.
Bourier et al. "Fiberoptic Contact-Force Sensing Electrophysiological Catheters: How Precise Is Technology?", Journal of Cardiovascular Electrophysiology, 28(1): 109-114, Published Online Oct. 24, 2016.
Canpolat et al. "Relationship Between Vitamin D Level and Left Atrial Fibrosis in Patients With Lone Paroxysmal Atrial Fibrillation Undergoing Cryoballoon-Based Catheter Ablation", Journal of Cardiology, 6991): 16-23, Published Online Aug. 21, 2016.
Caspi et al. "Modeling of Arrhythmogenic Right Ventricular Cardiomyopathy With Human Induced Pluripotent Stem Cells", Circulation: Cardiovscular Genetics, 6(6): 557-568, Published Online Nov. 7, 2013.
Cerit et al. "Association of Pre-Ablation Level of Vitamin D With Atrial Fibrillation Recurrence After Catheter Ablation", Europace, 19(9): 1586, Sep. 1, 2017.
Chierchia et al. "An Initial Clinical Experience With a Novel Microwave Radiometry Sensing Technology Used in Irrigated RF Ablation for Flutter", Academic Hospital Brussels, Belgium, 1 p. Jan. 1, 2011.
Crospon "Esophageal Treatment by Esoflip®", Crospon, Product Sheet, 4 P., 2017.
Crospon "Flip® Technology", Crospon, Product Sheet, 6 P., 2017.
Deno et al. "Measurement of Electrical Coupling Between Cardiac Ablation Catheters and Tissue", IEEE Transactions on Biomedical Engineering, 61(3): 765-774, Published Online Nov. 6, 2013.
Eyerly et al. "The Evolution of Tissue Stiffness at Radiofrequency Ablation Sites During Lesions Formation and in the Peri-Ablation Period", Journal of Cardiovascular Electrophysiology, 26(9): 1009-1018, Sep. 2015.
Gabriel "Compilation of the Dielectric Properties of Body Tissues at RF and Microwave Frequencies", Occupational and Environmental Health Directorate, Radiofrequency Radiation Division, Brooks Air Force Base, Texas, USA, Technical Report for the Period Sep. 15, 1993-Dec. 14, 1994, p. 1-16, Jan. 1996.
Gaspar et al. "Use of Electrical Coupling Information (ECI) in AF Catheter Ablation: A Prospective Randomized Pilot Study", HeartRhythm, 10(2): 176-181, Feb. 2013.
General Electric "CardEP: Streamlined Post-Processing for Enhanced Electrophysiology Procedures", General Electric Company, GE Healthcare, Product Description, 2 P., 2016.
Grace "Modifying PVI Lines to Incorporate Non-PV Targets fdentified by PreAblation Mapping with the AcQMap System: Update on the UNCOVER-AF Trial," EP Lab Digest, 17(5), May 2017, 5 pages.
Hilbert et al. "An Integrative Approach to Slow Pathway Modulation in a VNRT Using a Novel Ultra High-Density Electroanatomical Mapping System", Clinical Research in Cardiology. XP035518036, 104(8): 697-699, Published Online Mar. 31, 2015.
Ikeda et al. "Microwave Volumetric Temperature Sensor Improves Control of Radiofrequency Lesion Formation and Steam Pop", 33rd Annual Scientific Sessions, Heart Rhythm, Boston, MA, USA. May 9-12, 2012, Session: Role of Autonomies in Catheter Ablation, # AB13-05, May 10, 2012.
Ikeda et al. "Novel Irrigated Radiofrequency Ablation Catheter With Microwave Volumetric Temperature Sensor Predicts Lesion Size and Incidence of Steam Pop in Canine Beating Heart", 33rd Annual Scientific Sessions, Heart Rhythm, Boston, MA, USA, May 9-12, 2012, Poster Session III, # P03-53, May 10, 2012.
Jiang et al. "Association of Pre-Ablation Level of Potential Blood Markers With Atrial Fibrillation Recurrence After Catheter Ablation: A Meta-Analysis", Europace, 19(3): 392-400, Mar. 1, 2017.
Karim et al. "Surface Flattening of the Human Left Atrium and Proof-of-Concept Clinical Applications", Computerized Medical Imaging and Graphics, 38(4): 251-266, Jun. 2014.
Lardo et al. "Visualization and Temporal/Spatial Characterization of Cardiac Radiofrequency Ablation Lesions Using Magnetic Resonance Imaging", Circulation, 102(6): 698-705, Aug. 8, 2000.
Lemola et al. "Computed Tomographic Analysis of the Anatomy of the Left Atrium and the Esophagus. Implications for Left Atrial Catheder Ablation", Circulation, 110(24): 3655-3660, Published Online Nov. 29, 2004.
Lunak "12 510(k) FDA Summary for Public Disclosure", St. Jude Medical, Section 12, 6 P., Aug. 29, 2013.
McDowell et al. "Virtual Electrophysiological Study of Atrial Fibrillation in Fibrotic Remodeling", PLOS One, 10(2): e117110-1—e117110-16, Published Online Feb. 18, 2015.
Myronenko et al. "Non-Rigid Point Set Registration: Coherent Point Drift", Advances in Neural Information Processing Systems, NIPS, 19: 1009-1016, 2009.
Pappone "Carto 3", AF-Ablation, Arrhythmology and Cardiac Electrophysiology Department, 1 P., 2009.
Perazzi et al. "Panoramic Video From Unstructured Camera Arrays", Computer Graphics Forum, 34(2): 57-68, May 2015.
Piorkowski et al. "First in Human Validation of Impedance-Based Catheter Tip-to-Tissue Contact Assessment in the Left Atrium", Study of Clinical Results, Poster, Journal of Cardiovascular Electrophysiology, 20(12): 1366-1373, Published Online Jul. 7, 2009.
Ranjan et al. "Gaps in the Ablation Line as a Potential Cause of Recovery From Electrical Isolation and Their Visualization Using MRI", Circulation: Arrhythmia and Electrophysiology, XP055452459, 4(3): 279-286, Published Online Apr. 14, 2011.

(56) References Cited

OTHER PUBLICATIONS

Sanchez-Quintana et al. "Anatomic Relations Between the Esophagus and Left Atrium and Relevance for Ablation of Atrial Fibrillation", Circulation, 112(10): 1401-1406, Published Online Aug. 29, 2005.

Shoemaker et al. "Common Genetic Variants and Response to Atrial Fibrillation Ablation", Circulation: Arrhythmia and Electrophysiology, 8(2): 296-302, Published Online Feb. 14, 2015.

St. Jude Medical "Cardiac Mapping System / ECG. NSite™ NavX™", St. Jude Medical, Products Sheet, 22 P., 2017.

Ueberham et al. "Genetic ACE I/D Polymorphism and Recurrence of Atrial Fibrillation After Catheter Ablation", Circulation: Arrhythmia and Electrophysiology, 6(4): 732-737, Published Online Jul. 22, 2013.

Vandekerckhove et al. "Flutter Ablation With an Irrigated Catheter Using Microwave Radiometry Sensing Technology: First Report in Men", Sint Jan Hospital, Department of Cardiology, Bruges, Belgium, 1 P., Jan. 1, 2011.

Wang et al. "Association of the Angiotensinogen M235T Polymorphism With Recurrence After Catheter Ablation of Acquired Atrial Fibrillation", Journal of the Renin-Angiotensin-Aldosterone System, 16(4): 888-897, Published Online Aug. 3, 2015.

Wang et al. "Colon Unraveling Based on Electrical Field: Recent Progress and Further Work", Proceedings of the SP1E 3660 Medical Imaging '99: Physiology and Function From Multidimensional Images, San Diego, CA, USA, Feb. 1999, XP055479173, 3660: 125-133, May 20, 1999. Abstract, Sections 1, 2.2, 2.3, Figs.2, 3.

Wang et al. "Microwave Radiometric Thermoetry and Its Potential Applicability to Ablative Therapy", Journal of Interventional Cardiac Electrophysiology, 4(1): 295-300, Feb. 2000.

Wittkampf et al. "LocaLisa: New Technique for Real-Time 3-Dimensional Localization of Regular Intracardiac Electrodes", Circulation, 99(10): 1312-1317, Mar. 16, 1999.

Zhong et al. "On the Accuracy of CartoMerge for Guiding Posterior Left Atrial Ablation in Man", Heart Rhythm, 4(5): 595-602, Published Online Feb. 9, 2007.

Notification of Office Action and Search Report dated Nov. 1, 2021 From the State Intellectual Property Office of the People's Republic of China Re. Application No. 201780077003.7. (9 Pages).

\* cited by examiner

† cited by third party

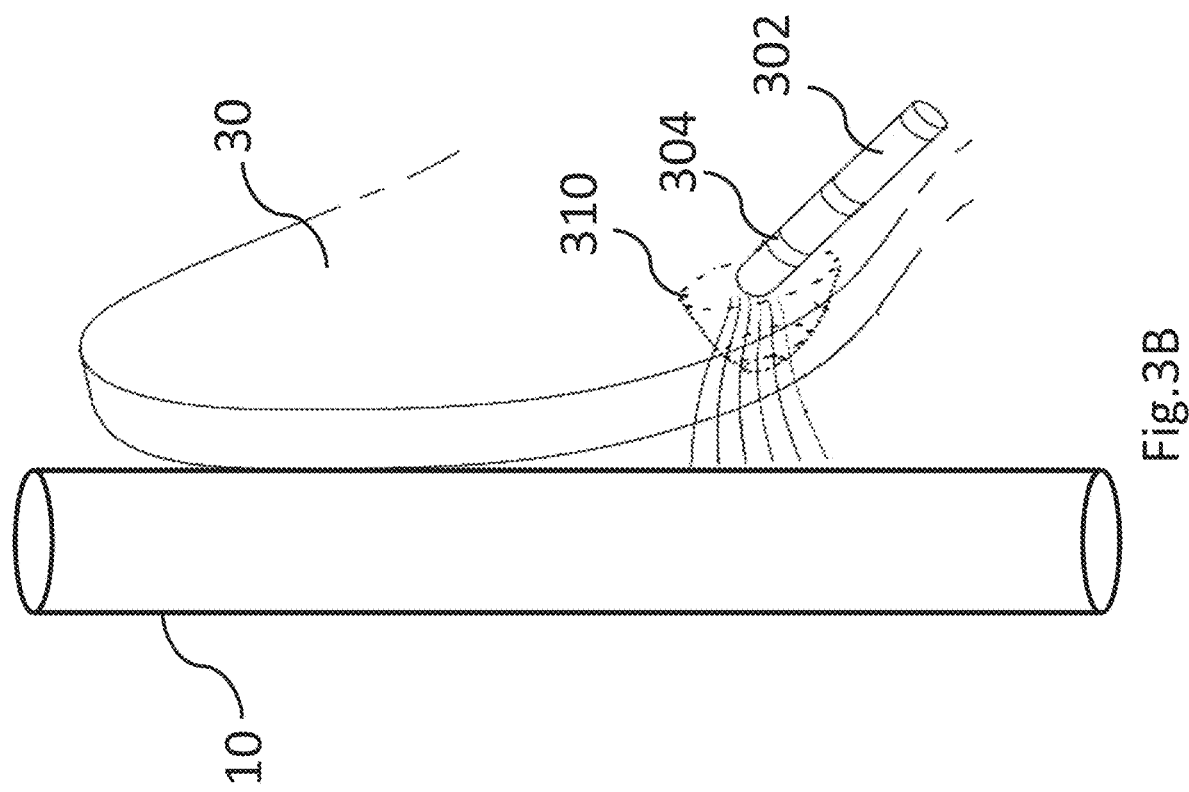

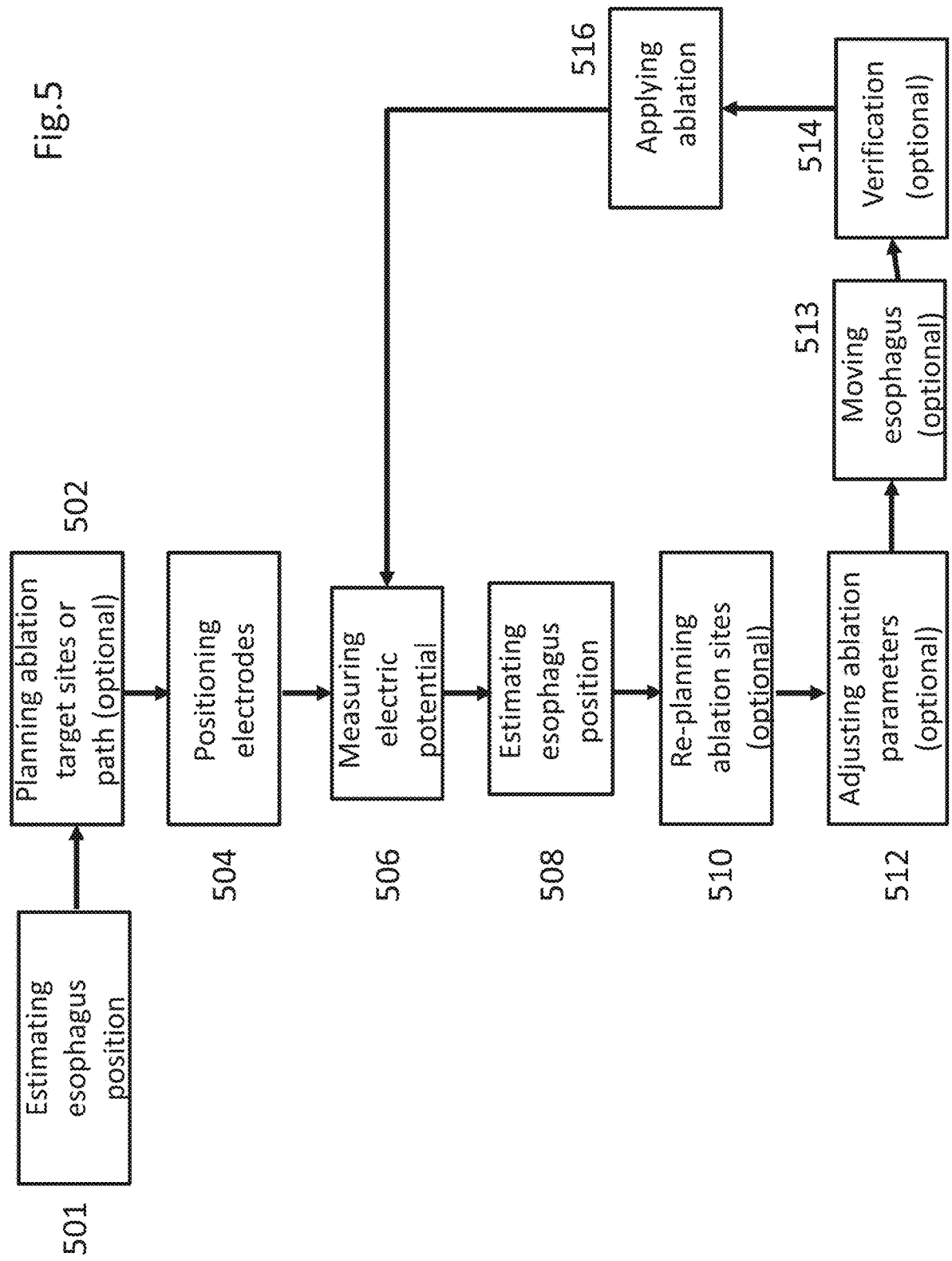

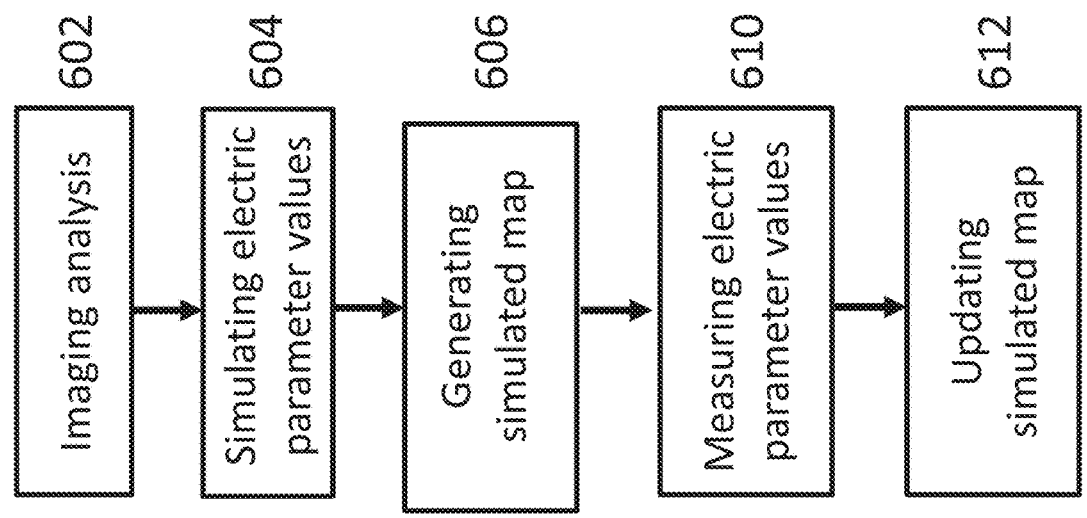

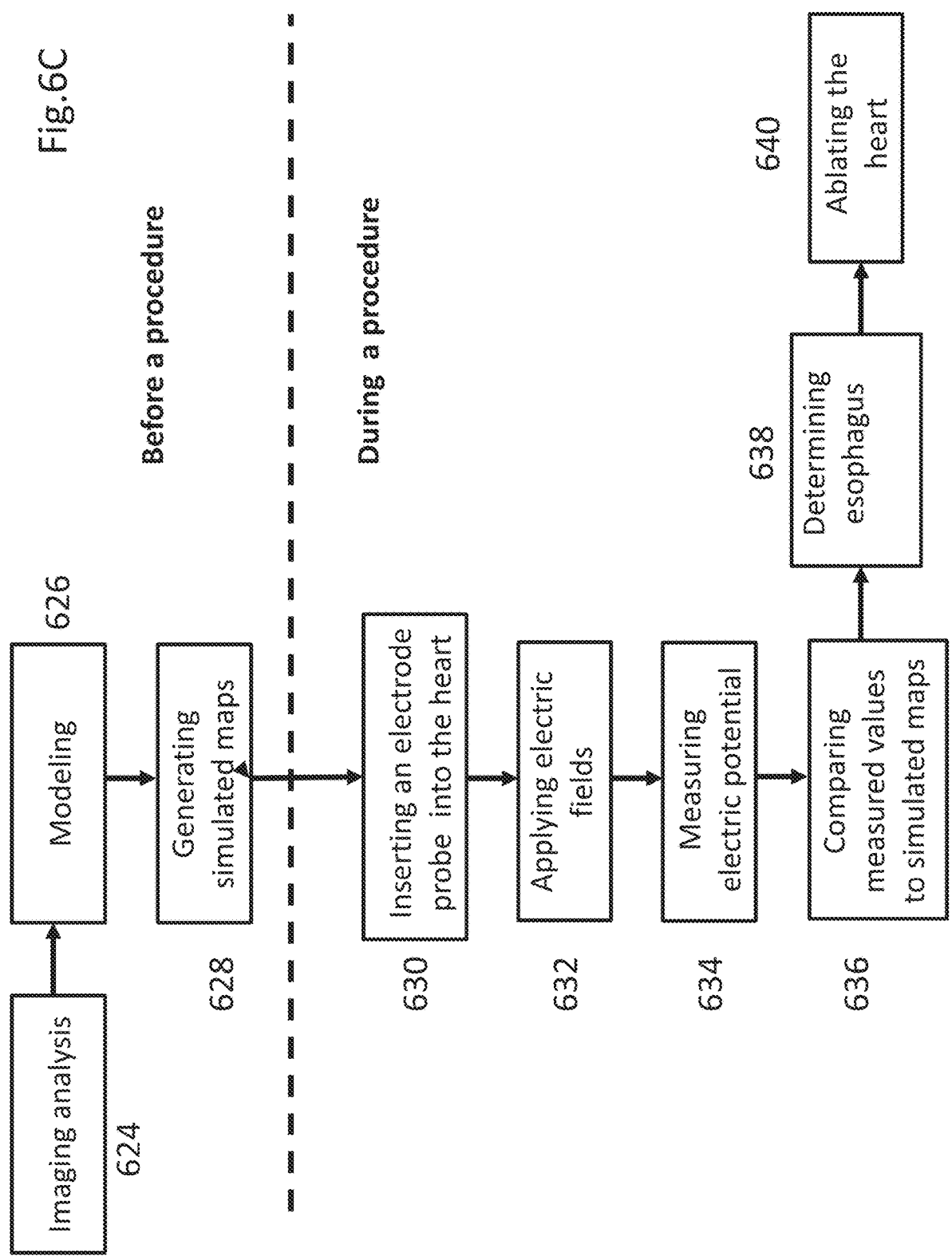

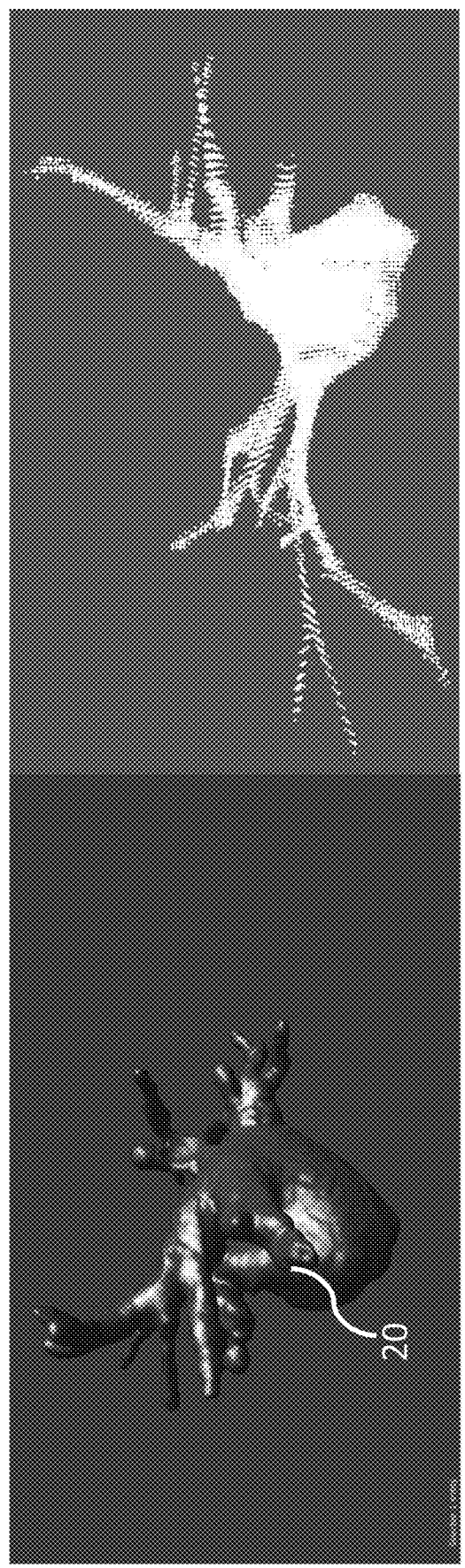

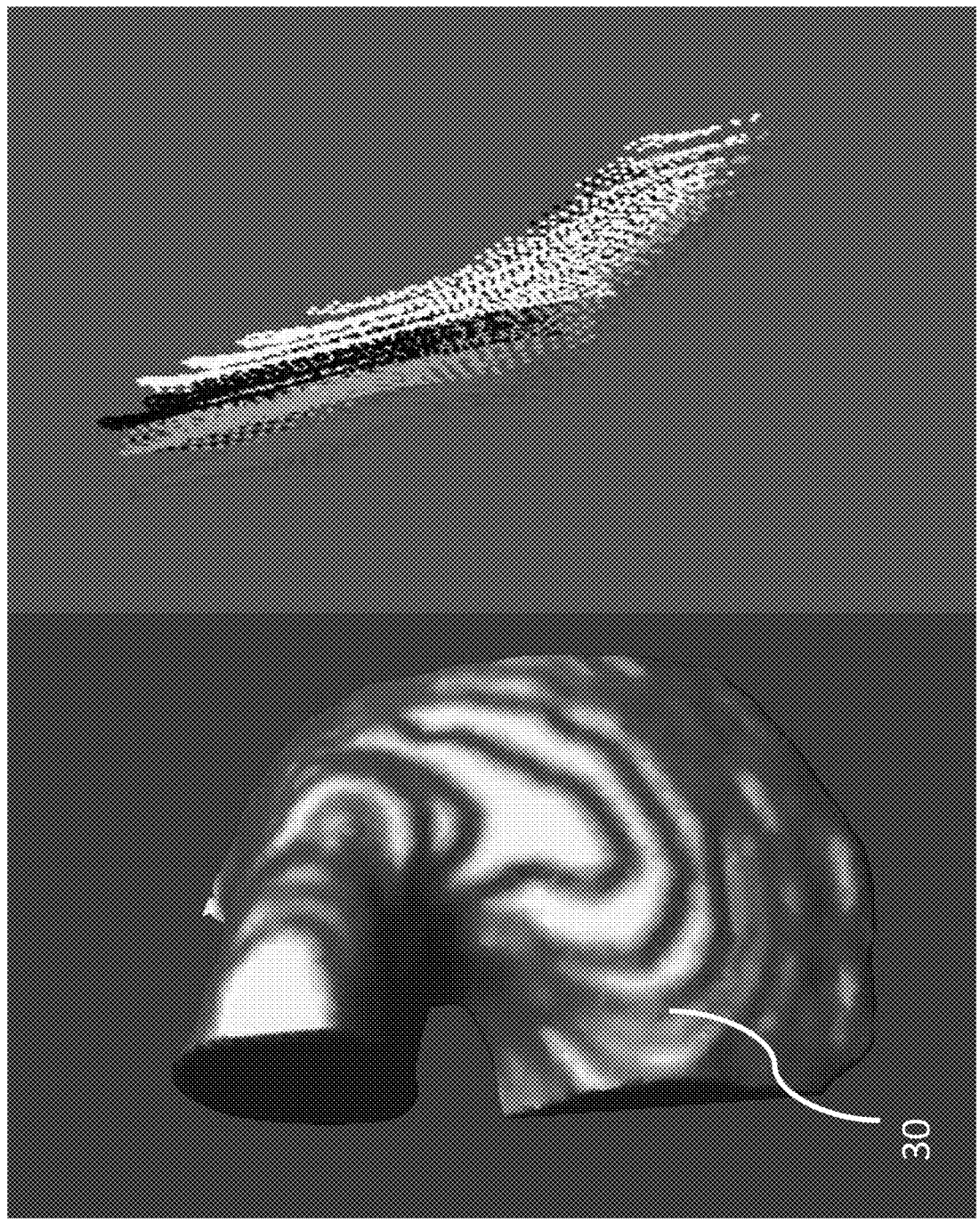

ESOPHAGUS POSITION DETECTION BY ELECTRICAL MAPPING

RELATED APPLICATIONS

This application is a National Phase of PCT Patent Application No. PCT/IB2017/057185 having International filing date of Nov. 16, 2017, which claims the benefit of priority under 35 USC § 119(e) of U.S. Provisional Patent Application No. 62/422,767 filed on 16 Nov. 2016, U.S. Provisional Patent Application No. 62/546,775 filed on 17 Aug. 2017 and U.S. Provisional Patent Application No. 62/445,433 filed on 12 Jan. 2017. The contents of the above applications are all incorporated by reference as if fully set forth herein in their entirety.

FIELD AND BACKGROUND OF THE INVENTION

The present invention, in some embodiments thereof, relates to a method for measuring electric parameters and, more particularly, but not exclusively, to a method for measuring electric parameters for estimating esophagus position.

U.S. Patent Application Publication No. 2008/0177175A1 describes an esophageal mapping catheter that is introduced into the esophagus and enables a physician to map the location of the Esophagus so as to avoid damaging the Esophagus during radio frequency (RF) ablation procedures.

SUMMARY OF THE INVENTION

There is provided, in accordance with some embodiments of the present disclosure, a method of estimating a spatial relationship between at least a part of a patient esophagus and a heart chamber, comprising: measuring at least one electric parameter at one or more positions within the heart chamber to obtain measured values; and estimating the spatial relationship based on the measured values.

In some embodiments, the estimating comprises estimating the spatial relationship between a treatment target site in the heart chamber and the esophagus.

In some embodiments, the method further comprises: generating an electric property map based on the measured values.

In some embodiments, the method further comprises: generating an anatomical map of the heart chamber or a portion thereof based on the measured values.

In some embodiments, the estimating further comprises identifying at least one region within the electric property map having deviations in the measured values resulted from the proximity of the esophagus to the heart chamber.

In some embodiments, the deviations are deviations of the electric property map from map values corresponding to the absence of an esophagus in proximity to the at least one region.

In some embodiments, the deviations are deviations of the electric property map toward map values corresponding to the presence of an esophagus in proximity to the at least one region.

In some embodiments, the electric property map comprises an electric potential map.

In some embodiments, the electric property map comprises an electric impedance map.

In some embodiments, the method further comprises: generating a measured electric property map based on the measured values; comparing the electric property map to at least one simulated electric potential map; identifying at least one region within the electric potential map generated based on the measured values, the at least one region having deviations resulting from a proximity of the esophagus to the heart chamber; wherein the estimating is based on the deviations.

In some embodiments, the deviations are deviations of the electric property map from map values corresponding to the absence of an esophagus in proximity to the at least one region.

In some embodiments, the deviations are deviations of the electric property map toward map values corresponding to the presence of an esophagus in proximity to the at least one region.

In some embodiments, the method further comprises: generating an electric property map based on the measured values; comparing the electric property map to one or more simulated maps of the electric property; and identifying one or more simulated electric property maps similar to the measured electric property map; wherein the estimating is based on the one or more simulated electric property maps identified.

In some embodiments, the identifying one or more similar maps comprises identifying one or more similar maps with a value difference aggregate below a threshold.

In some embodiments, the estimating is based on the identification of at least two similar maps.

In some embodiments, the method further comprises: determining whether the spatial relationship is a targeted spatial relationship.

In some embodiments, the method further comprises: indicating if the spatial relationship is not a targeted spatial relationship.

In some embodiments, the method further comprises: automatically suggesting an alternative target site if the spatial relationship is not a targeted relationship.

In some embodiments, the method further comprises: automatically suggesting at least one modification of an ablation protocol parameter if the spatial relationship is not a targeted spatial relationship.

In some embodiments, the method further comprises: stopping an ablation procedure unless human overrides, if the spatial relationship is not a targeted spatial relationship.

In some embodiments, the method further comprises: automatically suggesting to move the esophagus to an alternative position if the spatial relationship is not a targeted spatial relationship.

In some embodiments, the method further comprises: applying at least 3 electric fields to a body of the patient by at least 3 pairs of electrodes placed on the skin of the patient for determining a position of an electrode within the heart chamber; wherein the measuring at least one electric parameter comprises measuring an electric parameter of the fields by an electrode positioned within the heart chamber.

In some embodiments, the electrode positioned within the heart chamber is used both to estimate the position of the esophagus and for ablation.

In some embodiments, the measuring at least one electric parameter comprises measuring electric potential.

In some embodiments, the estimating comprises estimating that the esophagus is not within a certain range.

In some embodiments, the treatment target site comprises an ablation target site.

In some embodiments, the heart chamber comprises the left atrium.

In some embodiments, the spatial relationship comprises distance.

In some embodiments, the method comprises estimating an effect of a treatment in the heart chamber on the esophagus based on the spatial relation.

There is provided, in accordance with some embodiments of the present disclosure, a method of providing an indication to spatial relationship between at least a part of a patient esophagus and a heart chamber, comprising: receiving measurements of at least one electric parameter at one or more positions within the heart chamber to obtain measured values; generating a map of the heart chamber based on the measured values; estimating the spatial relationship based on the map; and providing an indication of the spatial relationship estimated.

In some embodiments, the map is an electrical parameter map.

In some embodiments, the map is an anatomical map.

In some embodiments, providing an indication comprises providing the map carrying an indication of the spatial relationship estimated.

In some embodiments, estimating the spatial relationship comprises identifying, at a wall of the heart chamber, electrical field bending indicative of an air-field tube behind the wall of the heart chamber.

In some embodiments, estimating the spatial relationship comprises identifying in the map a deformation indicative of an air-field tube behind the wall of the heart chamber.

There is provided, in accordance with some embodiments of the present disclosure, a method for estimating the position of at least part of the esophagus from within a heart chamber, comprising: measuring at least one electric parameter from within the heart chamber to obtain measured values; and estimating the position of the at least part of the esophagus based on the measured values.

In some embodiments, the method further comprises: generating an electric potential map based on measured values of the electric parameter, after the measuring; comparing the electric potential map to at least one simulated electric potential map; identifying at least one region within the electric potential map generated based on the measured values, the at least one region having variations resulted from a proximity of the esophagus to the heart chamber, based on the comparing; wherein the estimating is based on the variations.

In some embodiments, the method further comprises: generating an electric potential map based on measured values of the electric parameter, after the measuring; comparing the electric potential map to one or more simulated electric potential maps; identifying one or more similar maps of the simulated electric potential maps similar to the electric potential map generated based on measured values; wherein the estimating is based on the at least one simulated electric potential map identified.

In some embodiments, the method further comprises: determining whether the estimated position of the esophagus is a targeted position.

In some embodiments, the method further comprises: indicating if the estimated position is not a targeted position.

There is provided, in accordance with some embodiments of the present disclosure, a method for estimating from within a heart chamber a probability to affect at least part of the esophagus by treating the heart chamber, comprising: measuring at least one electric parameter from within the heart chamber; and estimating the probability to affect the at least part of the esophagus based on measured values of the electric parameter.

In some embodiments, the estimating comprises: estimating the probability to injure the esophagus.

In some embodiments, the method further comprises: generating an electric property map based on measured values of the electric parameter, after the measuring; wherein the estimating further comprises identifying at least one region within the map having variations in the measured values resulted from the proximity of the esophagus to the heart chamber.

In some embodiments, the electric property map comprises an electric potential map.

In some embodiments, the electric property map comprises an impedance map calculated from the electric potential map or from the measured values of the electric parameter.

In some embodiments, the method further comprises: generating an electric potential map based on measured values of the electric parameter, after the measuring; comparing the electric potential map to at least one simulated electric potential map; identifying at least one region within the electric potential map generated based on the measured values, the at least one region having variations resulted from a proximity of the esophagus to the heart chamber, based on the comparing; wherein the estimating is based on the variations.

In some embodiments, the method further comprises: generating an electric potential map based on measured values of the electric parameter, after the measuring; comparing the electric potential map to one or more simulated electric potential maps; identifying one or more similar maps of the simulated electric potential maps similar to the electric potential map generated based on measured values; wherein the estimating is based on the at least one simulated electric potential map identified.

In some embodiments, the method further comprises: determining whether the probability is higher than a targeted probability.

In some embodiments, the method further comprises: indicating if the probability is higher than a targeted probability.

In some embodiments, the method further comprises: stopping stop a procedure of the treating if the probability is higher than a targeted probability.

In some embodiments, the electric parameter comprises electric potential.

In some embodiments, the heart chamber comprises the left atrium.

In some embodiments, the spatial relationship is between the at least part of the esophagus and a target site for ablation.

There is provided, in accordance with some embodiments of the present disclosure, a device for estimating esophagus position, comprising: measuring circuitry configured to receive signal measurements of an electric parameter from an electrode probe navigating within a heart chamber; and control circuitry, configured to model the heart chamber based on the signal measurements, and to estimate a position of at least part of an esophagus adjacent to the heart chamber, based on the signal measurements.

In some embodiments, the device further comprises: an interface circuitry, wherein the interface circuitry generates an indication of esophagus position based on the estimation of the esophagus position.

In some embodiments, the device further comprises: a digital computer memory; wherein the control circuitry estimates the esophagus position by comparing a measured map constructed to associate the signal measurements with positions in the heart chamber to one or more reference maps, stored in the digital computer memory, wherein the reference maps associate predicted values of the electric parameter with the positions in the heart chamber.

In some embodiments, at least one of the reference maps is a simulated map.

In some embodiments, the simulated map also simulates effects of an esophagus at a simulated location on measurements of the reference map.

In some embodiments, the simulated map omits effects of any esophagus on measurements of the reference map.

In some embodiments, at least one of the reference maps is a map constructed using a measured map having a known position of the at least part of the esophagus adjacent to the heart chamber.

In some embodiments, the control circuitry estimates the esophagus position by comparing a measured map of the shape of the heart chamber constructed using the signal measurements to one or more reference maps of the shape of the heart chamber; wherein the measured map is constructed using a method that allows distortions of an electric field due to the presence of an esophagus to distort a shape of the measured map.

In some embodiments, at least one of the reference maps is a simulated map.

In some embodiments, the simulated map also simulates effects of an esophagus at a simulated location on a heart chamber shape of the reference map.

In some embodiments, the simulated map omits effects of any esophagus on heart chamber shapes of the reference map.

In some embodiments, at least one of the reference maps is a map constructed using a measured map having a known position of the at least part of the esophagus adjacent to the heart chamber.

In some embodiments, the control circuitry estimates the esophagus position using a template shape to match a shape of the measured map of the heart chamber.

In some embodiments, the measuring circuitry is connected to a catheter system configured to be at least partly placed within a heart chamber to measure the electric parameter.

In some embodiments, the device further comprises: at least one electrode connectable to the measuring circuitry; wherein the electrode is shaped and sized to be placed within a heart chamber to measure the electric parameter.

In some embodiments, the device further comprises a field generator is configured to deliver an energy field to a heart chamber through an electrode placed in the heart chamber based on the esophagus position of the at least part of the esophagus.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as measuring dielectric properties of a tissue might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A and 3B are schematic illustrations describing the positioning of an electrophysiological catheter probe at the left atrium for measuring electrical properties and/or for treating the tissue, according to some embodiments of the invention;

FIG. 5 is a flow chart describing a process for estimating spatial relationship between the esophagus and the heart combined with an RF ablation procedure, according to some embodiments of the invention;

FIG. 6A is a flow chart describing a process for generating and updating an electric parameter map, according to some embodiments of the invention;

FIG. 6C is a flow chart describing estimation of at least part of the esophagus by comparing measured electric parameter values to simulated maps, according to some embodiments of the invention;

FIGS. 7A-7I are images describing simulated electric parameter maps of the heart and the LA, according to some embodiments of the invention.

DESCRIPTION OF SPECIFIC EMBODIMENTS OF THE INVENTION

Figure 1A:
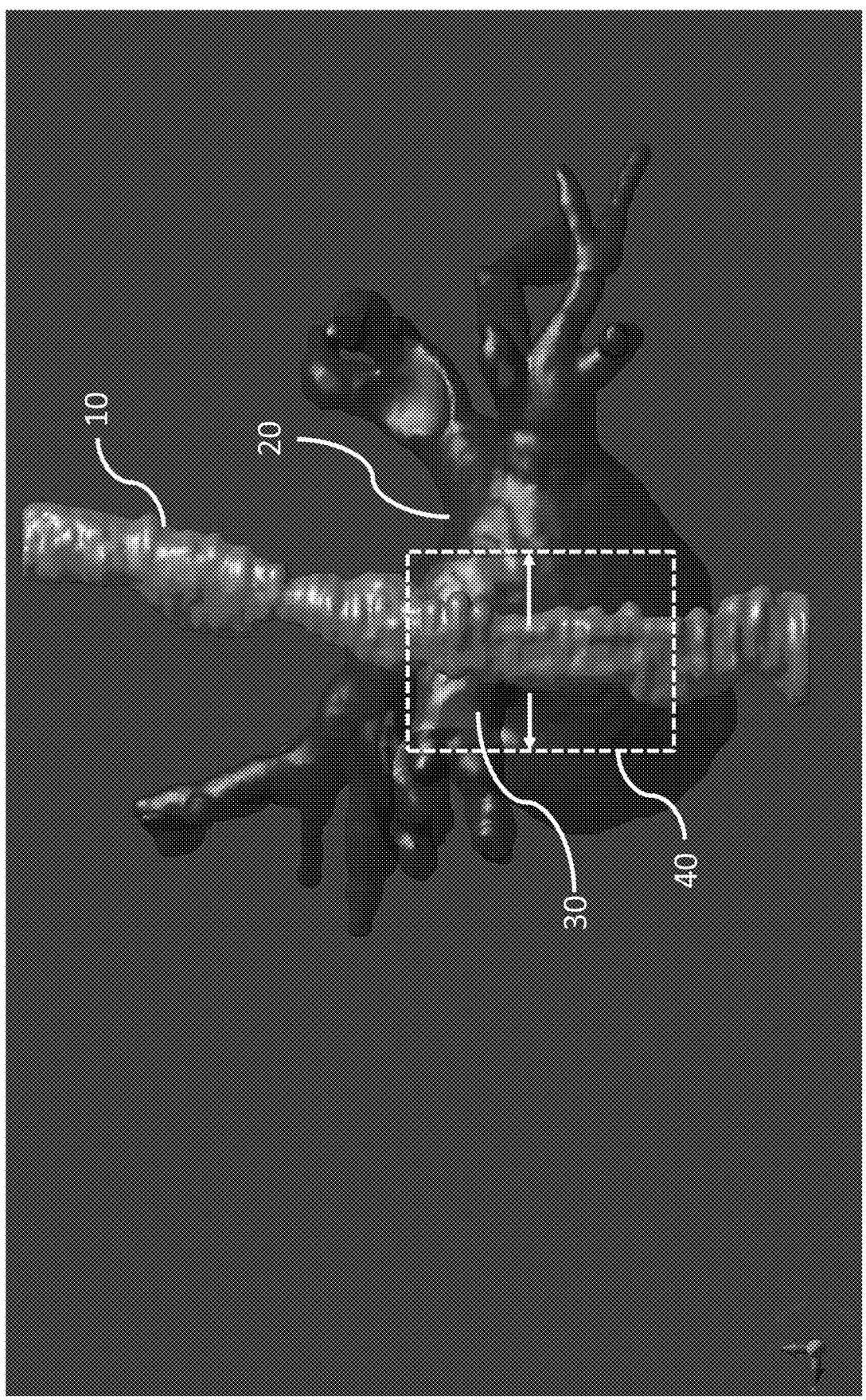
FIG. 1A is an image describing a typical spatial relationship between the heart and the esophagus.

The present invention, in some embodiments thereof, relates to a method for measuring electric parameters and, more particularly, but not exclusively, to a method for measuring electric parameters for estimating esophagus position.

An aspect of some embodiments of the present invention relates to estimating the position of at least part of the esophagus from within a heart chamber. In some embodiments, the position of at least part of the esophagus is estimated prior to a treatment, when the heart chamber is to be treated in a way (e.g., by heart tissue ablation using an ablation probe) that might affect the esophagus, if the distance between the esophagus and a treated site is too short. Estimation of the position of the esophagus, or the distance between the esophagus and a site to be treated, may allow planning the treatment not to injure the esophagus, and/or adjusting the treatment once it is estimated during the treatment that the distance between a site to be treated and the esophagus is not safe. For example, the treatment may be an ablation treatment using an ablation probe, and the ablation heat may cause burns in the esophagus if the latter is too close to an ablated site.

In some exemplary embodiments of the invention, estimation of esophagus position is used to guide the placement of an intra-cardiac treatment probe, e.g., to avoid damage to the esophagus during a treatment such as tissue ablation using the probe.

An aspect of some embodiments includes estimating, from within a heart chamber, a probability to affect the esophagus when treating a selected target site within the heart chamber. In some embodiments, a spatial relationship, for example distance and/or, angle between esophageal tissue and the treatment target site is estimated (or existence or lack of existence within a range of such). In some embodiments, estimating esophagus position and/or esophageal tissue proximity to a treatment target site allows to avoid or minimize an adverse effect of the treatment on the esophageal tissue, for example a site marked as a target for ablation. The estimation of the esophagus position may take place prior to the treatment and/or during the treatment, In some embodiments, the position of at least part of the esophagus is estimated by measuring at least one electric parameter, for example electric potential and/or impedance, from at least one and preferably from a multiplicity of positions within the heart chamber. In some embodiments, the position of the esophagus is estimated based on detected local value deviations, for example from expected values, and calculating a possible position of the esophagus that can generate these deviations. In some embodiments, the expected values are based on multiple measurements performed in multiple subjects. Alternatively, the position of the esophagus is determined by comparing a map generated based on the measured electric parameter values, to a map expected to have been generated. Herein, uses of the term "deviation" in conjunction with the indication of an esophagus position by measurement values should be understood to be deviation with respect to "expected values" and/or an "expected pattern" expected in the absence of an esophagus in proximity to the region from which measurement values are obtained. For example, the "expected pattern" is pattern expected in the case of the hypothesis that there is no esophagus in proximity. The deviation may be understood, for example, as a difference from an expected pattern. The deviation may more particularly be detected as a difference between a shape indicated by measurement values used to map a cardiac chamber and expected shape of the cardiac chamber.

Additionally or alternatively, the deviation is recognized by similarity to one or more patterns of measurement values that do indicate the proximity of an esophagus, and/or define a characteristic shape. The characteristic shape may be, for example, of a portion of a substantially cylindrical shape. The deviation may be recognized when such a cylindrical (or other characteristic shape) appears in a region where such a cylindrical shape is not expected in the absence of an esophagus in proximity.

In some embodiments, expected values relative to which deviation is assessed (using values individually, and/or patterns of values) are derived from multiple measurements performed in multiple subjects, in regions where the esophagus is not in proximity. The deviation is optionally assessed relative to a statistical summary of the expected values (e.g., average and standard deviation), relative to a collected large population of expected values (e.g., expressed in terms of an averaged distance of values from values obtained in individual members of the large population), and/or using another method, such as a supervised machine learning method using the expected values as inputs. Expected values can also be simulated, in some embodiments. In some embodiments, deviation is additionally assessed with respect to a large population of measurements at positions wherein the esophagus is in proximity to the measurement position. For example, such measurements (and/or simulations thereof) are used as input to a supervised machine learning algorithm. Accordingly, a deviation away from expected values or a pattern of values is additionally or alternatively a deviation toward values or a pattern of values which is expected in proximity to an esophagus. In this context, deviating away from expected values means resembling less closely by a suitable metric and deviating toward expected values means resembling more closely by a suitable metric. In some embodiments, a magnitude of difference may be a suitable metric.

In some embodiments, assessment of deviation of a pattern of values is based on use of a map generated from measured electric parameter values. For example, the position of the esophagus is estimated by comparing similarity of a map generated based on the measured electric parameter values, to a map having a pattern expected to have been generated in the absence of an esophagus in proximity. In some embodiments, the similarity may be compared by average of magnitude of distance after registration, or other suitable metric. The comparison allows identifying at least one pattern that deviates between the two maps and may result from the proximity of the esophagus. In some embodiments, for example, the pattern deviations comprise cylindrically-shaped deviations resulting from the proximity of the cylindrically-shaped esophagus. The term "cylindrically-shaped" should be understood to refer to a substantially cylindrical shape or to a portion of such shape.

In some embodiments, the expected pattern is based on patterns determined using multiple electrical parameter measurements performed in many subjects. For example, in some embodiments, electrical mapping is performed for multiple subjects as described in relation to FIG. 1B, yielding shapes of heart chamber walls. Heart wall shapes used to derive one or more patterns as references for evaluating deviation (away from and/or toward particular patterns) are based on, for example, which positions the electrode catheter is able to visit before stopped by a heart chamber wall, which positions yield measurements indicating wall contact (e.g., changes in local dielectric properties), and/or another feature of the electrical measurements. For example U.S. Provisional Patent No. 62/546,775; filed 17 Aug. 2017, the contents of which are included herein by reference in their entirety, relates to a method of electrical mapping using patterns in local electrical field gradients which may indicate shapes of more remote chamber surfaces and potentially the existence of features laying beyond such as the esophagus.

Optionally, maps used to provide patterns for evaluation of deviation in a particular case are at least partially simulated. In some embodiments, the position of the esophagus in a particular case is estimated by finding similarity between one or more simulated maps that were generated based on different esophagus positions, and a map generated based on the measured electric parameter values. In some embodiments, similarity is detected using algorithms, for example value difference aggregate algorithms which summarize the measured values and determine similarity based on a difference between a value difference aggregate and a threshold. In addition, statistical calculations and modifications of the measured electric parameter values are optionally performed, for example to allow their comparison to simulated maps or simulated values. Optionally, the esophagus position is estimated by comparing locally measured dielectric values to predicted dielectric values that were calculated based on a structural map (i.e., a map which describes shapes of surfaces) and/or an anatomical map (i.e., a structural map which additionally includes representation of tissue volumes, optionally including representation of tissue type and/or properties) of the measured region.

The esophagus 10, for example as shown in FIG. 1A, is a muscular tube, often partially filled with air, that descends anteriorly to the vertebral column through the superior and posterior mediastinum, posteriorly to the heart 20. When the esophagus 10 passes near the heart 20, at least part of the esophagus is in close contact or in a close proximity to the posterior wall 30 of the left atrium (LA). Additionally, the esophagus 10 moves laterally (as symbolized by the arrows) and can transiently move to various positions within rectangle 40. The close proximity to the heart 20 is one of the reasons why esophageal injury is a potential complication after intraoperative or percutaneous transcatheter ablation of the posterior aspect of the LA. To prevent or minimize this complication, it may be beneficial to estimate the position of at least part of the esophagus in respect to the posterior wall of the left atrium, and more particularly, in respect to a site to be ablated. To estimate an atrium-esophagus distance (A-E distance), an electrode probe, for example an electrophysiological (EP) catheter probe is inserted, in some embodiments, into the LA for measuring an electric parameter. Herein "A-E distance" refers to any estimate of distance between a particular position on a heart chamber wall (e.g., left atrial wall) and the esophagus. In some embodiments, the estimate is qualitative, for example "located behind" or "not located behind" ("behind" meaning "adjacent to the particular position at a position exterior to the heart chamber"). In some embodiments, the estimate is in terms of a functional and/or safety issue, for example "located too close to safely ablate" or not. In some embodiments, the distance is estimated as a distance from the particular position to a position of the atrial wall behind which the esophagus is estimated to be located, e.g., a position around which the esophagus is centered, or a position behind which a nearest side of the esophagus is positioned. Optionally, a distance (i.e. gap) between the esophagus and the heart wall and/or inner surface of the heart wall generally is also estimated for positions of the heart wall behind which the esophagus lies. For example, deviations may be smaller when the esophagus is spaced from the heart wall. However, estimation of the esophagus being located behind a particular region of cardiac wall (or not) generally provides an A-E distance resolution sufficient for uses such as avoiding ablation that may put the esophagus at risk for damage, or limiting ablation energy (i.e. power and/or time of ablation) to avoid putting the esophagus at risk.

Alternatively, the electrode probe is inserted into other heart cavities, for example the right atrium (RA), left ventricle (LV) or the right ventricle (RV). Optionally, the catheter probe is inserted into a blood vessel, for example the coronary sinus.

In some particular embodiments of the invention, the electric parameter, measurements used to estimate the A-E distance are measured during application of an electric field to the body. An electrode optionally measures electric potential and/or another electric parameter at different locations within the heart chamber in response to the applied electric field. In some embodiments, the measured electric potential values reflect dielectric properties of tissues and organs surrounding the measurement site, for example cardiac tissue, muscle tissue and esophageal tissue. Esophageal tissue in particular may create a relatively large deviation in local dielectric properties (compared to normal conditions in its absence), because the esophagus often contains one or more pockets of air, which has a much larger electrical impedance than tissue. The muscular tissue of the esophagus itself (surrounding the air) has dielectric properties which are distinguishable from other tissue types which may be found adjacent to the heart, in particular lung. Lung also is filled with air, but the structure of the air pockets is much more finely divided by non-muscular lung tissue having a lower impedance, making it dielectrically distinct from the esophagus. Measurements of the electric potential generated in response to the applied electric field allow, in some embodiments, estimation of the A-E distance.

In some embodiments, the electric field is applied by at least one electrode, or at least one pair of electrodes placed on the outer surface of the skin, for example 1, 2, 3, 4 pairs of electrodes. Alternatively or additionally, the electric field is applied by at least one electrode placed within the body. Optionally, the electric field is applied by at least one electrode placed within the heart chamber, for example by at least one electrode located on the EP probe.

In some particular embodiments of the invention, the measured electric parameter values are used to generate a map, for example an electric property map. In some embodiments, the electric property map comprises electric potential map, impedance map, and/or currents map. In some embodiments, the generated map is used to estimate the position of at least part of the esophagus, for example by identifying patterns associated with the proximity of esophageal tissue to the heart. In some embodiments, the identified patterns comprise deviations in the size, shape or electric parameter values. Alternatively, the generated map is compared to one or more simulated electric parameter maps which were prepared by simulating electric parameter values based on estimated positions of the esophagus. In some embodiments, results of the comparison are used to estimate the position of part of the esophagus and/or a spatial relationship between esophageal tissue and at least one measurement site or between the esophageal tissue and the LA.

In some particular embodiments of the invention, the position within the heart chamber of the electrode used for measuring the electric parameter values, is determined using electric measurements. Additionally or alternatively, the position of the electrode is determined using another method, for example using magnetic methods (e.g., sensing from a magnetic coil positioned within crossing magnetic fields).

In some embodiments, a magnetic field, rather than or in addition to the electric field, is applied to the body for measuring said distance, for example by at least one magnetic coil.

In some embodiments, when the electrode position is determined, the electric parameter is measured, for example to detect deviations in electric parameter values, for example compared to expected values.

In some particular embodiments of the invention, the simulated map is prepared by simulating predicted electric potential values, as if they are measured at different locations within a heart chamber. In some embodiments, at least one simulated map is prepared based on imaging analysis results which describe the position of the esophagus and a spatial relationship between the esophagus and the heart. The imaging may be, for example, imaging by projection X-ray, CT, MRI, ultrasound, remote electrical field-based imaging, or another imaging method). The position and spatial relationship inferred from the imaging analysis are the position and spatial relation at the time the image was taken. Additionally, the simulated map is based on estimated dielectric properties of the tissues surrounding a predicted measurement site within the heart chamber. In some embodiments, several simulated maps are prepared which are based on the current position of the esophagus and on at least one additional predicted location of the esophagus. In some embodiments, the at least one simulated map is prepared prior to the insertion of the electrode into the heart chamber. In some embodiments, by comparing the measured electric parameter values or the electric potential or impedance map which are based on these measurements to at least one simulated map, the position of at least part of the esophagus can be estimated.

In some particular embodiments of the invention, an ablation target site is selected based on the estimated location of the esophagus or based on the estimated spatial relationship between an optional ablation target site and esophageal tissue. In some embodiments, if the estimated spatial relationship between an optional target site and esophageal tissue is not at a desired spatial relationship (e.g., the A-E distance is too short) then an indication is delivered to a user, for example to an expert who navigates the EP probe or the ablation probe. Optionally, an alternative target site is automatically suggested by the system in response to a received indication.

In some embodiments, if the estimated spatial relationship is not a desired spatial relationship, then the treatment procedure, for example an ablation procedure is stopped. Alternatively, if the spatial relationship is not a desired spatial relationship or if there is a risk that the esophagus will move too close to the heart chamber, then the esophagus can be moved to a desired position or to be fixed, for example by insertion of an object into the esophagus and maneuvering or fixating the esophagus position. In some embodiments, a desired spatial relationship, for example a desired distance or a desired A-E distance, comprises a spatial relationship between an ablation target site and at least part of the esophagus that permits safe ablation at the target site without affecting the esophagus, or that the effect on the esophagus is an allowed or safe effect. Optionally, if there are no deviations in the electric parameter values from expected values in the absence of an esophagus in proximity, or if the electric parameter map resembles a simulation run with no esophagus in the vicinity of the heart, the existence of a targeted spatial relationship (or safe A-E distance) may be determined.

In some particular embodiments, the probability to affect the esophagus when treating a selected target site within the heart chamber is estimated, for example by measuring an electric parameter from within the heart chamber. In some embodiments, estimating the probability to affect the esophagus is based on detecting deviations in the measured values from expected values in the absence of an esophagus in proximity to the heart chamber. Alternatively, estimating the probability to affect the esophagus is based on finding similarity between the measured values and one or more simulated maps, for example as described in FIG. 6B. In some embodiments, if the probability to affect the esophagus is higher than a maximum allowable probability, then an indication is delivered to a physician or to an expert. Optionally, if the probability to affect the esophagus is higher than a maximum allowable probability then the treatment procedure is stopped. The maximum allowable probability may be set according to safety requirements, and in some embodiments may be, for example, 5%, 1% or lower.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Method of Estimating the Position of an Electrode Within the Heart

Figure 1B:
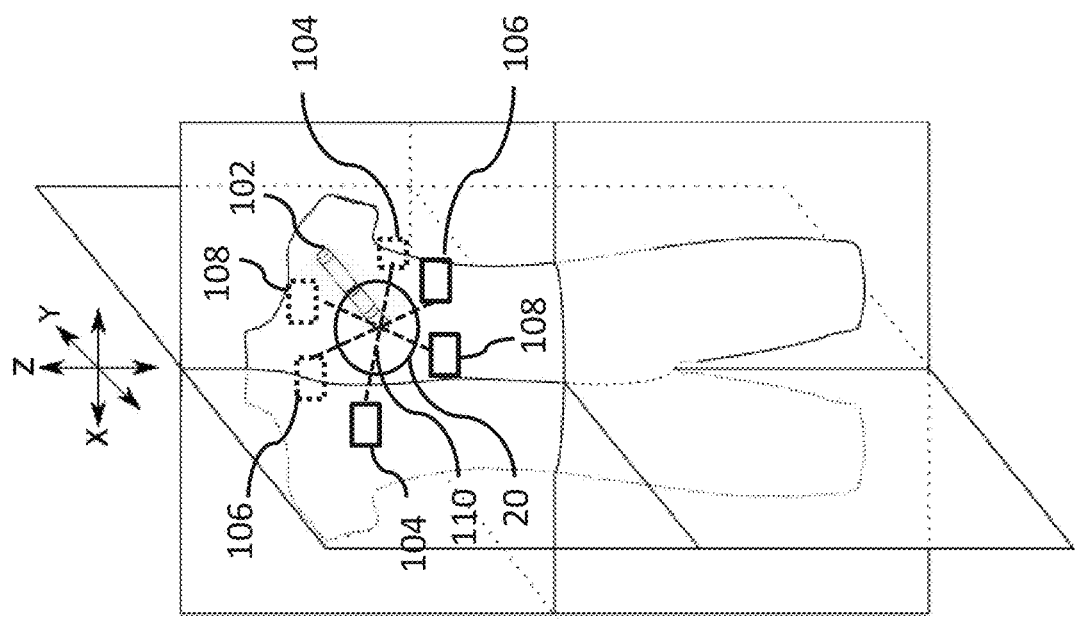
FIG. 1B describes an arrangement of electrodes for application of electric fields, according to some embodiments of the invention.

Reference is now made to FIG. 1B depicting an arrangement for electrodes for application of electric fields, according to some embodiments of the invention.

In some embodiments, electrical field-guided navigation of a probe 102 is performed within a region of the body, for example within heart 20 (FIG. 1A). The navigation comprises assessment of electrode probe 102 position in space based on electrical field measurements. The fields as a whole are not necessarily homogenous or mutually orthogonal, but do include field components falling along the orthogonal spatial axes. Herein, unless otherwise noted, the X and Y fields are considered to cross in the transverse plane of the body. Optionally, a Z field crosses both of these fields with a component approximately orthogonal to both the X and Y fields. Optionally, as shown for example in FIG. 1B, the X field extends across the left and right directions of the body, while the Y field extends between ventral and dorsal positions. Optionally—and particularly for sensing in the thoracic and abdominal cavities—body surface electrode positions are selected so that fields cross the body in about the cardinal directions, between electrode positions bracketing the region of interest as closely as possible.

In some embodiments, electrode pairs 104, 106 and 108 deliver an electric field 110 to the body, for example by attaching the electrodes to selected locations on the outer surface of the skin. In some embodiments, each electrode pair delivers an electric field with a different frequency. There may also be crossing of fields between non-paired electrodes; for example, in some embodiments, at least one electrode of electrode probe 102 measures electric potential of applied electric field 110 by one or both electrodes of electrode pair 104. In some embodiments, the measured electric parameter is a parameter of the applied electric field. In some embodiments, the position of the electrode probe within the heart can be determined based on the changes in electric field generated in different frequencies and the measured electric potential values.

In an "ideal" body, having a dielectric constant that is the same throughout the body, and between electrodes of infinite separation, the electric field propagates in straight lines between each two electrodes generating a time-varying electrical field therebetween, and is attenuated at a constant rate between the electrodes. Thus, in ideal body there may be a linear relationship between electrical parameters measured by an electrode, and the position of the electrode within the ideal body, and a high-fidelity map may be generated from electrical readings using linear transformations between the electrical readings and the positions. However, in a real body with finite electrode separation, the field is curved, and moreover the dielectric constant changes in space (at least because different tissues have different dielectric properties). Linear mapping between electrical readings and electrode positions results in a low-fidelity map in this situation. However, non-linear transformations, (for example, as described in U.S. Provisional Patent No. 62/445,433; filed Jan. 12, 2017) may provide maps with higher fidelity to the actual spatial arrangement being mapped.

In some embodiments, the frequencies of the electrical field used are in the range of 40 kHz to 2 MHz. Optionally, the number of frequencies used is 10 or fewer frequencies. Optionally, the frequencies are distributed (for example, distributed evenly) throughout the full range of frequencies chosen. Optionally, frequencies chosen are concentrated in some particular frequency range. Applied voltages are preferably in the safe range for use in humans, for example, 100-500 millivolts, and/or a current of 1 milliamp or less (a typical body resistance is about 100Ω). Resulting field strengths are in the range, for example of a few millivolts per centimeter; for example, 5 mV/cm, 10 mV/cm, 20 mV/cm, or another larger, smaller, or intermediate value. Based on requirements for data acquisition, sensing time is optionally about 10 msec per measurement (or a longer or shorter period, for example, about 100 msec, or 1 second), for embodiments including fast automated switching of frequencies and/or electrode pairs.

Exemplary Methods for Estimating Esophagus Position

Figure 6B:
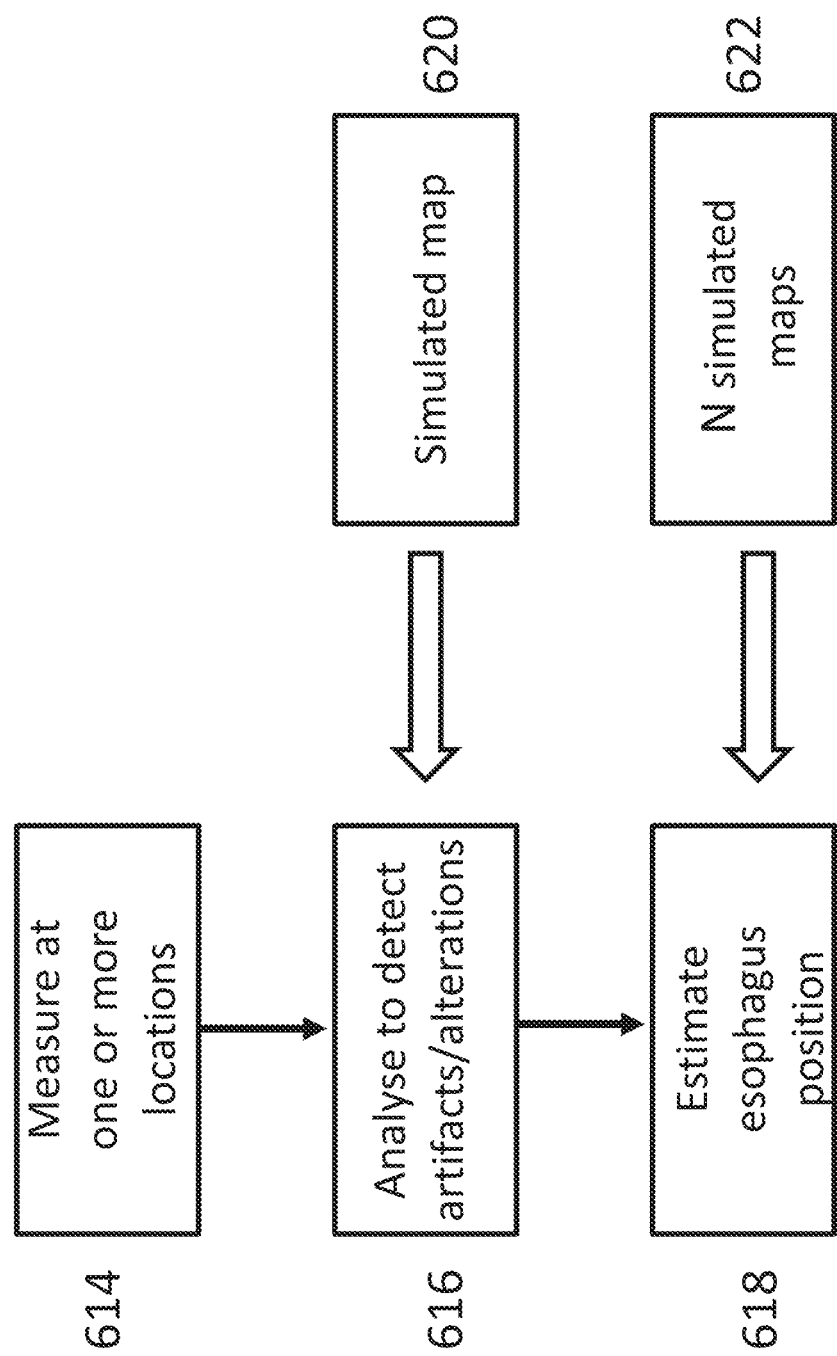
FIG. 6B is a flow chart describing methods for estimating a position of at least part of the esophagus, according to some embodiments of the invention.

Reference is now made to FIG. 6B, depicting methods for estimating the position of at least part of the esophagus, according to some embodiments of the invention.

According to some exemplary embodiments, an electrode probe is inserted into a heart chamber, for example into the LA and at least one electrode of the probe measures at least one electric parameter from at least one and preferably from a multiplicity of locations within the heart chamber at 614, while moving to map the heart chamber. Optionally, the electrode measures the electric parameter, for example electric potential, when contacting the heart chamber wall.

According to some exemplary embodiments, the position of at least part of the esophagus at 618 is estimated by analyzing the measured values of the electric parameter at 616 and detecting deviations from measurement values expected in the absence of an esophagus in proximity. These deviations result from the actual proximity of at least part of the esophagus to one or more of the measurement locations. Alternatively, the measured electric parameter values are compared to a simulated map of electric potential or impedance values, for example to detect altered measured electric parameter values compared to the simulated map. In some embodiments, the position of the esophagus is estimated, for example by calculating how different positions of the esophagus would produce the altered electric parameter values compared to the simulated values. In some embodiments, the measured electric parameter values are compared to a structural and/or an anatomical map of the measured region, for example to identify deviations between the measured values to expected values based on the organ and tissue types surrounding the one or more measurement locations.

According to some exemplary embodiments, the measured electric parameter values are compared to simulated electric potential or impedance maps 622 to find a one or more similar maps. In some embodiments, based on the position of the esophagus in the one or more similar maps, the position of the esophagus at the time of measurement can be estimated at 618.

According to some exemplary embodiments, the position of the electrode probe within the heart chamber is estimated based on application of an electric field or a magnetic field to the body, and then the position of the esophagus is estimated based on dielectric values of the tissue measured locally by at least two electrode of the electrode probe. In some embodiments, the measured dielectric values are analyzed to identify variation caused by esophageal tissue proximal to the measurement location, for example, according to the electrode position we expect to measure dielectric values of a muscle but instead the electrode measured dielectric properties of a different tissue. Optionally the measured dielectric values produce a shape which is different for the expected shape, based on the position of the electrode.

Exemplary Method for Estimating Esophagus Position

In some embodiments, the position of the esophagus is estimated before the ablation treatment to make a determination of proximity of the esophagus to a targeted treatment location. Such proximity may be related to a likelihood of esophagus injury from the treatment, and estimating the proximity in advance may allow the physician to prevent such esophagus injury, for example, by changing the ablation plan, or causing the esophagus to move (e.g., by asking the patient to swallow several times). Thus, according to some exemplary embodiments, the position of the esophagus is estimated before an ablation treatment, in order to prevent esophagus injury usually caused by the energy used for ablation, if the esophagus is too close to the ablation sight. Reference is now made to FIG. 6C depicting a method for estimating esophagus position by comparing measured electric potential values to simulated maps, according to some embodiments of the invention.

According to some exemplary embodiments, a patient undergoes an imaging procedure, for example CT, MRI or ultrasound of the whole body or of a selected body region at 624. In some embodiments, the imaging analysis is used for estimating the position of tissues and/or organs, for example the position of the esophagus and/or the position of the heart.

According to some exemplary embodiments, based on the results of the imaging procedure, a modeling procedure is performed at 626. In some embodiments, the modeling procedure comprises modeling the electrical properties of the body or a selected body region, for example by assigning tissue specific electrical properties to tissues and/or organs based on the results of the imaging procedure. The modeling optionally also includes modeling of particular conditions of electrode placement (e.g., body surface electrode placement) and use; for example, electrode position, electrode size, electrical field frequency, and/or electrical field voltage.

According to some exemplary embodiments, several simulated maps are generated at 628. In some embodiments, each map describes simulated electric potential that will be measured within at least part of the heart chamber, for example at least part of the LA when positioning the esophagus at different locations. In some embodiments, in each simulated map the esophagus is placed at a different spatial relationship, for example in a different distance from the LA. Optionally, at least one simulated map is generated by simulating electric potential values of the LA when there is no esophagus, for example to simulate electric potential values of the LA when there is no effect by the esophagus on the electric potential values.

According to some exemplary embodiments, during an ablation procedure, an electrode probe is inserted into the heart chamber, for example into the LA at 630. In some embodiments, the electrode probe includes at least one electrode, for example for application of an ablating energy and/or for measuring at least one electric parameter, for example electric potential and/or impedance.

According to some exemplary embodiments, once the electrode probe is positioned within the heart chamber, electric fields are applied to the body at 632. In some embodiments, the electric fields are applied by at least 3 electrode pairs that are attached to the outer surface of the skin. In some embodiments, the electrode pairs are positioned at selected locations on the skin. Optionally, the selected locations were used during the generation of the simulated electric potential maps at 628. In some embodiments, the intensity and/or the duration and/or the frequency of the applied electric fields were used during the generation of the simulated electric potential maps at 628.

According to some exemplary embodiments, during the application of the electric fields, the at least one electrode placed within the heart chamber measures electric potential, for example to map the electric potential of at least part of the heart chamber at 634. In some embodiments, the electrode measures electric potential at one or more locations within the heart chamber. Optionally, the electrode measures electric potential at one or more locations by contacting the heart chamber wall. In some embodiments, the measured electric parameter values are converted into impedance values.

According to some exemplary embodiments, the measured electric potential values are compared to the simulated maps at 636. In some embodiments, the measured electric potential values are compared to the simulated maps for example, to identify one or more simulated maps that are similar to the measured electric potential values. In some embodiments, the measured electric potential values are analyzed to generate a map of at least part of the heart chamber and then the map is compared to simulated maps, for example to identify one or more similar regions.

According to some exemplary embodiments, the position of the esophagus is estimated at 638. In some embodiments, the relative position of the esophagus is determined based on the identified similarity between the measured electric potential values and one or more of the simulated maps, as discussed at 636. In some embodiments, since each of the simulated maps is generated based on an estimated position of the esophagus, and based on the effect of the estimated position on the simulated electric potential values, finding similarity between the measured values and one or more simulated maps allows for example, to estimate the position of the esophagus. In some embodiments, the relative position of the esophagus is estimated using the estimated position of the esophagus that was used in the generation of the similar one or more simulated maps.

According to some exemplary embodiments, once the position of the esophagus is determined, at least one electrode of the electrode probe delivers treatment energy, for example RF energy to ablate the cardiac tissue at 640. In some embodiments, before ablating the tissue the at least one electrode that is used for ablation is positioned at an ablation target site that is verified to also be in a spatial relationship, for example larger than a minimal allowable distance (e.g., minimum safe distance to avoid damage), from the estimated position of the esophagus. Optionally, an ablation path which comprises at least two ablation target sites is selected based on the estimated position of the esophagus, before initiating the ablation procedure.

Exemplary Method for Estimating Esophageal Position

Figure 2:
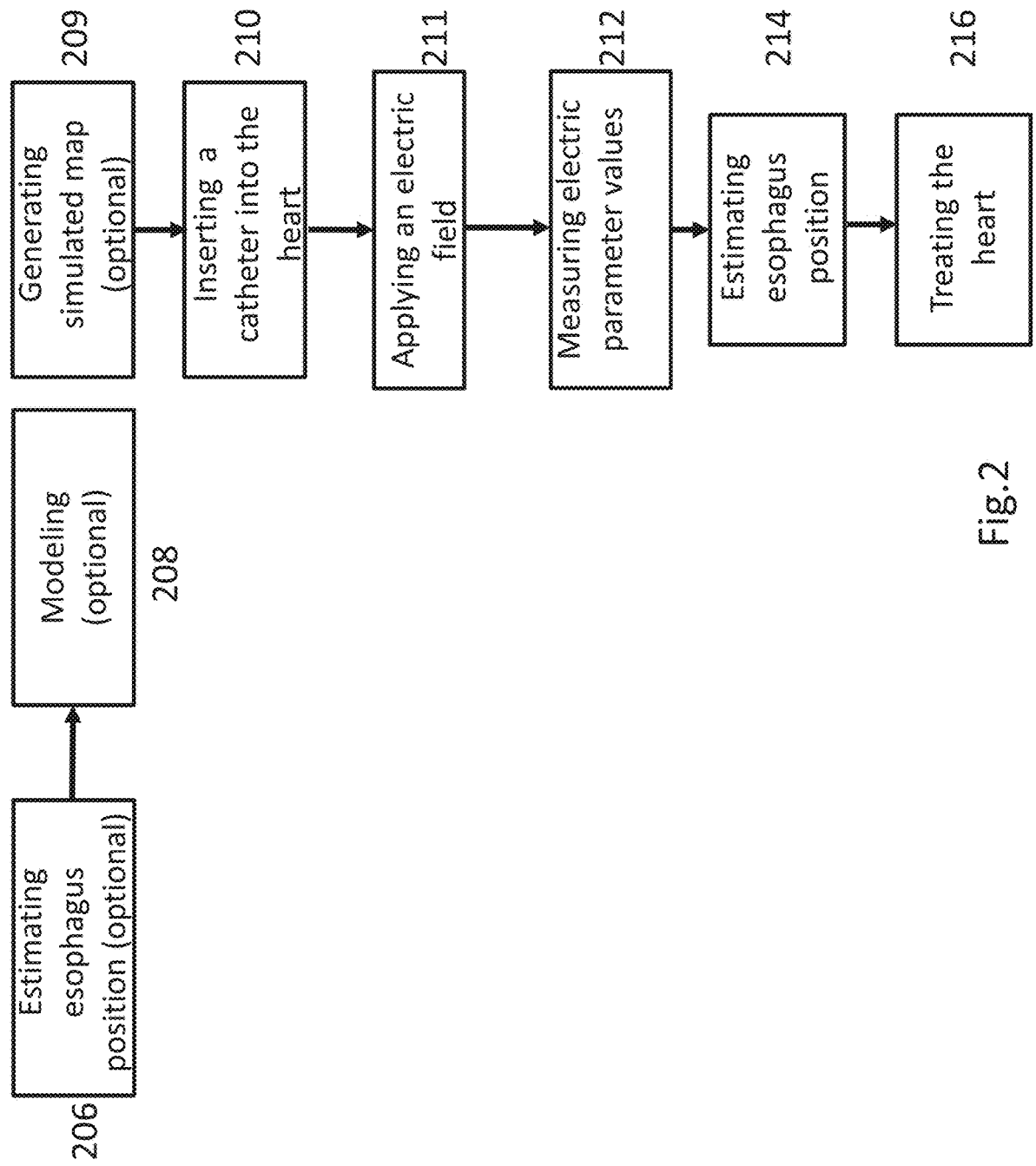
FIG. 2 is a general flow chart describing a method for treating the heart based on estimation of esophagus position, according to some embodiments of the invention.

Reference is now made to FIG. 2 depicting a method for treating the heart based on estimation of esophagus position, according to some embodiments of the invention. In some embodiments, the position of the esophagus is estimated prior to ablation treatment, for example, to minimize or eliminate adverse effects of the treatment on esophageal tissue.

According to some exemplary embodiments, the position of the esophagus is first roughly estimated based on analysis of an image of at least part of the heart and adjacent organs, at 206. The image may include both the heart or a portion thereof, and a portion of the esophagus in vicinity of the heart. This rough estimate is improved in later stages of the method. The imaging may be, for example magnetic resonance imaging (MRI), computed tomography (CT) and/or ultrasound.

According to some exemplary embodiments, the imaging results are then used to model the imaged region of the body by assigning electric properties to different tissues and/or organs demonstrated in the imaging results, at 208. Additionally, imaging comprises imaging the insertion of a catheter probe into the heart and placing at least one electrode pair, used for electric field application, at selected locations on the skin.

According to some exemplary embodiments, at least one simulated electric potential or impedance map is generated at 209. This simulated map is to be compared with a measured map to improve the estimation of the esophagus position at 214. In some embodiments, the simulated map is based on the modeling performed at 208. In some embodiments, the simulated map is generated by predicting electric potential or impedance values expected to be measured by an electrode at different locations within a heart chamber, for example within the LA of the heart. In some embodiments, at least one simulated map is generated based on the estimated position of the esophagus as estimated at 206. In some embodiments, at least one additional simulated map is generated, each based on a corresponding position of the esophagus. In some embodiments, the simulated maps are based on the imaging analysis results and on estimates of dielectric properties of tissues and/or organs surrounding the heart, for example dielectric properties that were assigned at 208.

According to some exemplary embodiments, at least one measuring electrode, for example an electrode of an EP catheter probe is inserted into a cavity of the heart, for example into the LA at 210, for measuring at least one electric parameter from at least one and preferably from a multiplicity of locations within the cavity. In some embodiments, the electrode is placed in contact with a cardiac tissue, or is found in a close proximity to the tissue. In some embodiments, the electrode probe is navigated into the heart chamber or into the blood vessel based on the imaging analysis used for the position estimation at 208. In some embodiments, the electrode measures electric potential when an electric field is applied. Optionally, impedance values are calculated from the measured electric potential values. In some embodiments, the electric potential or impedance measured at different locations inside the LA allows estimating the position of the esophagus outside the LA due to the effect of the esophagus on the electrical field developed inside the LA.

According to some exemplary embodiments, an electric field is applied by at least one electrode at 211. Alternatively or additionally, a magnetic field is applied. Alternatively or additionally, the electrode is in contact with a tissue outside of the heart chamber, for example with the outer surface of the skin. In some embodiments, the electric field is applied based on parameters of an electric field application protocol which includes for example, the electric field frequency and/or the electric field intensity.

According to some exemplary embodiments, at least one measuring electrode measures an electric parameter, for example electric potential from within the heart chamber or blood vessel at 212, when an electric field is applied at 211. Optionally, impedance values are calculated from the measured electric potential values. In some embodiments, the electrode measures the electric parameter while moving within the heart chamber or blood vessel. In some embodiments, the electrode measures the electric parameter in the whole volume of the chamber, for example the LA. Optionally, the electrode measures the electric parameter while contacting the walls of the heart chamber or the blood vessel. In some embodiments, the electrode measures the electric parameter at regions that are close to a desired ablation target site, and/or at regions that are close to at least part of the esophagus. In some embodiments, if patient is awake and cooperative, swallowing manipulation can allow an expert performing the procedure to detect esophagus and assist in verification electrical mapping diagnostic.

According to some exemplary embodiments, the measured electric parameter values are used to estimate the position of at least part of the esophagus at 214, for example by identifying deviations in the measured values compared to estimated values, which reflect an estimated position of the esophagus. In some embodiments, the measured electric parameter values are analyzed and optionally used to generate an electric potential or impedance map. In some embodiments, the generated map is used to estimate the position of at least part of the esophagus by identifying regions in the map that demonstrate the effect of a proximal esophageal tissue.

In some embodiments, the generated map is compared to at least one simulated map, for example a simulated map that was generated at 209, to identify a one or more similar simulated maps. In some embodiments, since at least one simulated map is based on a predicted position of the esophagus, finding similarity between a map which is based on measured values and a simulated map, provides an indication regarding the position of at least part of the esophagus in the time of measurement.

In some embodiments, based on the estimated esophagus position, at least one treatment target site or a treatment target path is selected by the system or by an expert performing the procedure. In some embodiments, selection of a treatment target site or the treatment target path is guided to avoid delivering energy within the heart chamber at positions that are close enough to the esophagus to raise a risk for injuring the esophagus.

According to some exemplary embodiments, energy for a treatment, for example RF energy for an ablation, is applied to at least one selected target site of the cardiac tissue at 216, based on the estimated esophagus position as described at 214. In some embodiments, the target site is selected considering its spatial relationship to the esophagus. Optionally, the target site is selected based on the probability of the treatment energy to affect at least part of the esophagus. In some embodiments, the treatment energy is applied by at least one electrode of the EP catheter probe.

According to some embodiments, before each application of treatment energy, the electric parameter is measured and the position of the esophagus is estimated, for example as described at 212 to 214, to verify that the esophagus position did not change during the treatment at 216.

Figure 3A:
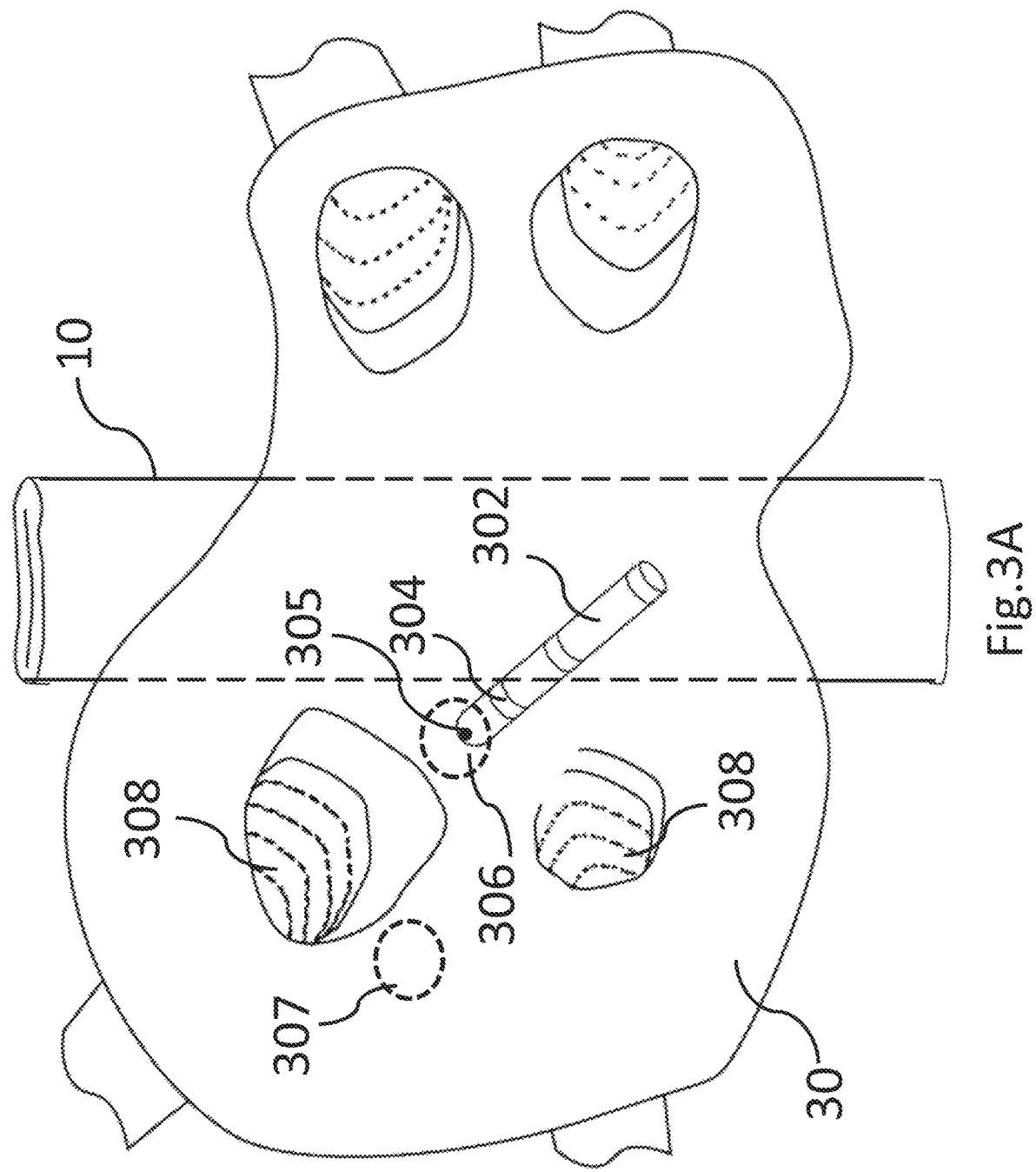

Example of Finding Relative Probe and Esophagus Positions from Within the Left Atrium Reference is now made to FIGS. 3A and 3B depicting the positioning of an electrode at different locations in the LA, for example for measuring electric potential, according to some embodiments of the invention.

According to some exemplary embodiments, an electrode probe, for example electrode probe 302 is inserted into a heart chamber, for example the LA 30. In some exemplary embodiments, the electrode probe 302 moves within the LA and/or in contact with the LA 30 wall, for example at target site 306. Optionally, target site 306 is a selected target site for application of a treatment, for example an RF ablation treatment. In some embodiments, target site 306 is in a close proximity to the pulmonary veins 308. In some embodiments, target site 306 is selected based on results of an imaging analysis and/or based on an electric potential or an impedance map of the region. Optionally, target site 306 is selected based on an estimated position of at least part of the esophagus.

According to some exemplary embodiments, at least one electrode of the electrode probe 302 measures at least one electric parameter within the LA 30, for example at a multiplicity of locations proximal to target site 306, and optionally other positions near which the esophagus may be positioned. Optionally, the electric parameter is measured prior to initiation of a treatment and/or during the treatment and/or after the treatment, for example application of treatment energy at target site 306.

According to some exemplary embodiments, application of treatment energy, for example RF energy to the cardiac tissue may lead to esophagus injury in cases where the treatment target site is proximal to esophageal tissue. According to some exemplary embodiments, the measured electric parameter of the tissue allows, for example to estimate the proximity of at least part of esophagus 10 to target site 306. Alternatively or additionally, the measured electric parameter allows, for example to determine whether application of treatment energy at target site 306 will injure esophagus 10, or the probability of such injury; or if this probability is small enough, for example, in reference to a safety threshold. In some embodiments, if the target site is proximal to at least part of the esophagus 10, and/or if application of an electric field at target site 306 is predicted to affect the esophagus 10, then, optionally, an attempt is made to move the esophagus, for example, by encouraging swallowing, or manual manipulation. Additionally or alternatively, an alternative target site for the treatment, for example target site 307 is selected, for example, automatically suggested. Target sites are optionally modified through the modification of a planned line of ablation; for example, a planned line of ablation is shifted to avoid a region where it would otherwise pass too close to an estimated position of the esophagus. Individual sites for ablation along the line may then be adjusted according to the new line of ablation, for example, planned so that they create an unbroken transmural line of ablation. The line of ablation can be shifted, for example, toward a pulmonary vein being electrically isolated by ablation. In some embodiments, at least one protocol parameter of the treatment energy application is modified, as part of the modification of an ablation site and/or line of ablation; for example the intensity (e.g., power and/or duration) of the treatment energy or the duration of the treatment is optionally modified.

In some embodiments, an electrode probe in the LA, measures electric potential or impedance, for example to determine the position of the electrode probe within the LA based on measured electric potential and/or impedance values and produces a map of corresponding electrode positions and measured values. Optionally, the determined correspondences of electrode positions with measured values are used to determine the position of the same or a different electrode probe which measures electric potential for estimating esophagus position as described herein. In some embodiments, an ablation probe is also an electrode probe which uses the determined correspondences of electrode positions with measured values to locate, e.g., ablation sites. The same electrode probe may be used for all three functions (map production, esophagus position estimation, and ablation), all three functions may be performed by separate probes, or the functions may be performed in any suitable combination by another plurality of probes.

Exemplary System for Estimating the Presence of the Esophagus

Figure 4A:
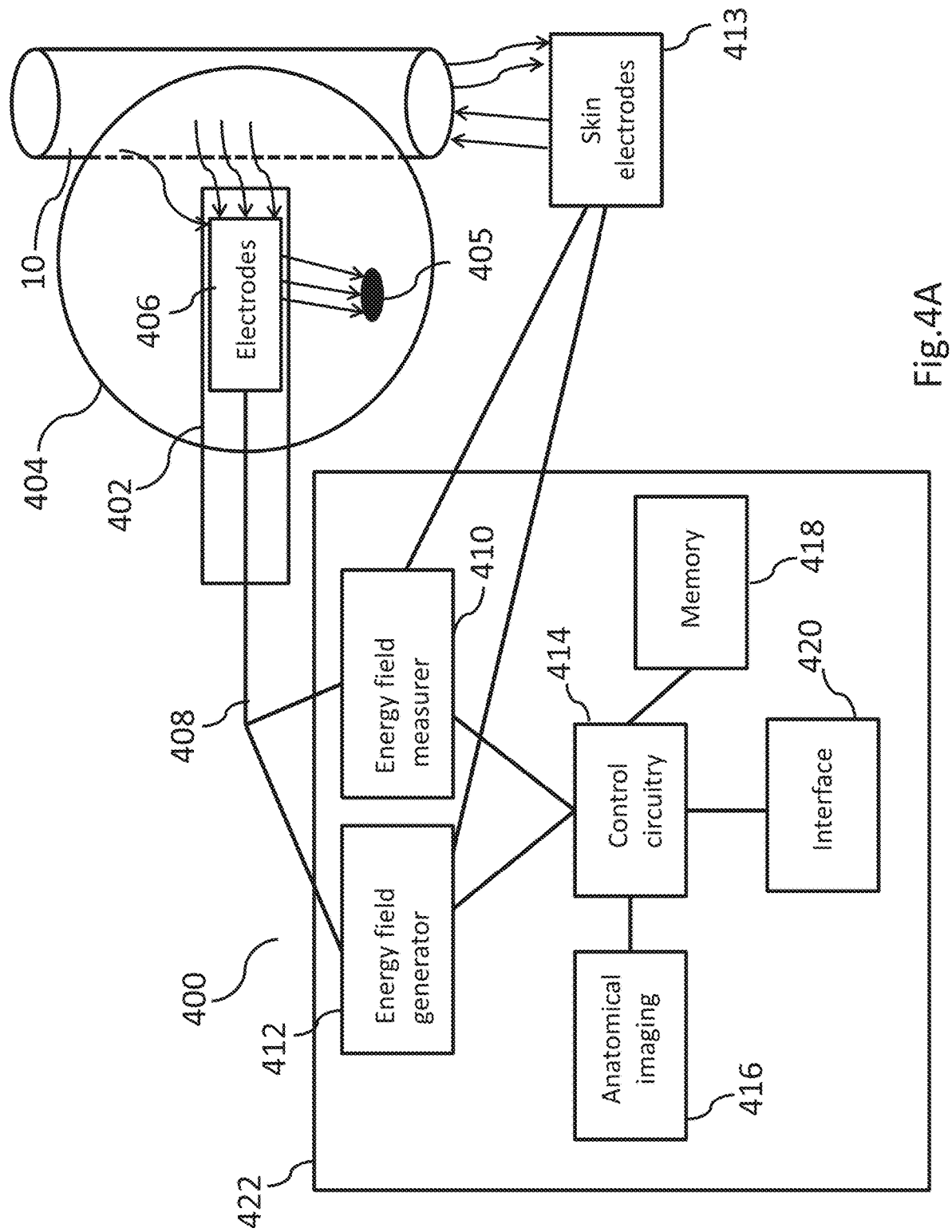
FIG. 4A is a block diagram of a device for measuring electrical properties from within the heart and for treating the tissue, according to some embodiments of the invention.

Reference is now made to FIG. 4A depicting a block diagram of a system for estimating the presence of at least part of the esophagus, according to some embodiments of the invention.

According to some exemplary embodiments, an electrode probe, for example catheter probe 402, is inserted into a heart chamber 404 (depicted body parts such as heart chamber 404 and esophagus 10 are not part of the system itself, but rather illustrated to help in an understanding of how the system components relate to one another and to functioning of the system). In some embodiments, catheter probe 402 comprises electrodes 406 with electrode contacts on the outer surface of catheter probe 402. In some embodiments, catheter probe electrodes 406 measure electrical parameters of one or more electrical fields generated within heart chamber 404, for example, parameters of electric potential and/or impedance at one or more frequencies.

According to some exemplary embodiments, at least one electrode of electrodes 406 is configured to apply treatment energy, for example to target site 405. In some embodiments, the treatment energy is delivered using an electric field, a thermal device, and/or radio-frequency transmission. Optionally the electrode is configured to ablate the tissue, for example by RF ablation.

According to some exemplary embodiments, the catheter probe 402 and/or electrodes 406 are connected by wiring 408 to an electric parameter measurer 410 component of device 400. Optionally, electric parameter measurer is configured to measure electric potential. In some embodiments, electric parameter measurer 410 receives the measured electrical signal from at least one electrode of electrodes 406, and optionally modifies the received signal for example, by amplifying and/or filtering the received signal.

According to some exemplary embodiments, electric parameter measurer 410 is connected to at least one additional electrode, for example skin electrode 413. In some embodiments, at least one skin electrode 413 comprises 1, 2, 3, 4, 5, 6, or 8 electrodes. Optionally, skin electrode 413 comprises at least one pair of electrodes, for example 2 pairs, 3 pairs, or 4 pairs.

According to some exemplary embodiments, electric parameter measurer 410 is connected to control circuitry 414. In some embodiments, control circuitry 414 is connected to treatment energy generator 412, which is configured to generate treatment energy, for example an electric, thermal or acoustic field. In some embodiments, the field generator is connected to electrodes 406 and/or to skin electrodes 413, for example to deliver the generated treatment energy to the tissue.

According to some exemplary embodiments, at least one electrode of electrodes 406 is positioned in close contact or adjacent to a cardiac tissue and measures at least one electric parameter of the tissue and/or surrounding tissues. The probe is preferably moved to measure at a multiplicity of locations, in order to build up a map of the region, optionally while measuring at a rate, e.g., of about 100 Hz. In some embodiments, the field generator 412 generates an electric field and delivers the electric field through at least one skin electrode 413 to the skin. In some embodiments, at least one electrode of electrodes 406 measures the electric parameter after the electric field is delivered by skin electrode 413.

According to some embodiments, control circuitry 414 estimates the position of at least part of the esophagus based on electric parameter values, for example electric potential values that were measured by electrodes 406 and/or skin electrode 413. Optionally, the presence of the esophagus is estimated based on analysis of the measured electric parameters results of MRI, CT, or ultrasound imaging analysis procedures.

According to some exemplary embodiments, control circuitry 414 estimates the position of at least part of the esophagus by generating a measured map based on the measured values of the electric parameter, and comparing this measured map to one or more reference maps that map expectations related to the esophagus in different places (including, optionally, in a place where it does not affect the measurements). Two main groups of embodiments of these two types of map will now be discussed in turn.

The embodiments of the first group rely on an assumption that all maps (measured and reference) assign values of the electrical parameter (e.g., voltage and/or impedance) to a common underlying anatomy, and if different values of the electrical parameter are associated to same anatomical places in different maps, this difference may be indicative of difference in the location of the esophagus. Thus, identifying the esophagus uses knowledge regarding which values were measured at different locations in heart chamber 404.

The embodiments of the second group rely on an assumption that all maps (measured and reference) result from a given mapping transformation transforming electrical values into anatomical structures; and differences between anatomies represented by the maps are indicative to where the esophagus is. Thus, identifying the esophagus requires comparing shapes of anatomical maps of heart chamber 404.

In the first group of embodiments, the measured map comprises measured values of one or more electrical field properties (for example, electric potential and/or impedance at one or more frequencies of one or more electrical fields induced through a mapped region of tissue), stored in correspondence with respective positions within the mapped region of tissue. The positions may be determined, for example, as described in relation to the second group of embodiments described below, or by another method; for example, magnetic sensing; or medical imaging using ultrasound and/or X-ray. In one such embodiment, the measured map may be generated by registering measured values of an electrical parameter to a pre-acquired image of the heart chamber. For example, measured voltage values may be registered to the pre-acquired image, and impedance values associated with the voltage values may be assigned to locations in the pre-acquired image based on the registration between voltages and locations.

The reference maps, in the first group of embodiments, comprise values of simulated and/or previously recorded electrical field properties (for example, electric potential and/or impedance at one or more frequencies of one or more electrical fields induced through a mapped region of tissue) stored in a digital computer memory 418 in association with respective positions at which the values occur. Optionally, each of the reference maps are generated by simulating values expected for the electrical parameter (e.g., for the impedance) based on the pre-acquired image used in determining positions for the reference maps, and an assumption of an esophagus missing, or located in a certain location in respect to the pre-acquired image.

The reference maps stored in memory 418 optionally include association between some portions of heart chamber 404 and different positions of the esophagus in the different maps (optionally no esophagus at all, which is explained separately further below). Simulated maps are generated, for example, as described in relation to block 209, herein. Additionally or alternatively, reference maps are generated from previously recorded data (e.g., in other subjects, where the position of the esophagus was known).

Comparison of the measured map to the reference map, in the first group of embodiments, optionally comprises identifying to what reference map the simulated map is most similar. For example, position-to-position (and optionally throughout the mapped volume, not necessarily just near the chamber wall), map values are compared, and the comparison that results in the smallest cumulative difference (or other metric of similarity) in a relevant portion of the maps indicates the most similar reference map. The esophagus position in the most similar reference map is then used as the estimated position of the esophagus. The "deviation" caused by the esophagus in this case may be understood as the portion of the most-similar reference map which is different from the way it is shown in reference maps with the esophagus missing, or located sufficiently distant not to affect the measurements.

Additionally or alternatively, a reference map used in a comparison is a map generated without any esophagus at all, for example by simulation, by the combination of suitable non-esophagus portions of a pool of maps obtained from previously recorded data (e.g., in other subjects), by the combination of enough maps with the esophagus in different positions that the esophagus "averages out", or another suitable method. The reference map should be well-registered to the measured map, for example by suitable distortions to align landmark features such as major apertures (blood vessels) and the like. A simulation based on the patient's own anatomy (for example, as determined using an MRI image) is preferable; however reference map data from other patients is optionally used by registering suitable portions of the reference maps data to a scaffold provided by imaging of the patient's own anatomy. Since the position of the esophagus is generally constrained, e.g., to a particular side of a heart chamber, the registration may be somewhat simplified to a matter of registering just the wall on that side. Then a difference between the reference map and the measured map is determined, for example, by subtraction of corresponding values. A region of the map showing large differences from similarity is then a candidate for the estimated position of the esophagus.

In the second group of embodiments, the measurement map is used in a form that defines an inner surface of heart chamber 404, and/or the boundaries of a cluster of measurement positions constrained by the inner surface so that they delimit an interior volume of heart chamber 404. For example, the measurement map may be generated by transforming the measurements using a given mapping transformation into anatomical structures. The reference map may be generated by transforming reference data by the same given mapping transformation. More generally, a measurement map in the form of a surface shape can be generated by several different methods.

One method uses impedance measurements of three crossed electrical fields having different frequencies, with each electrical field effectively establishing a spatial axis. Then measurements of a particular set of three voltage values correspond to a particular position in 3-D space. The surface shape of the heart chamber 404 may then be determined from the limits of the positions which can be visited within a well-explored heart chamber 404. The surface shape may additionally or alternatively be determined by measurements that indicate contact with a wall of the heart chamber, for example a change in impedance and/or force which is measured upon contact and/or near contact. Optionally, corrections for non-orthogonality and/or non-linearities help to improve the correspondence between the actual heart chamber 404 shape, and a shape determined from the three-field mapping values. However, if corrections for the effects of esophagus position are not explicitly provided, this mapping method may lead to errors in shape determination, due to distortion of the electrical field in the vicinity of the esophagus (particularly if the esophagus is gas filled). That error may be used as one source of a basis for esophagus position estimation.

Another method of determining surface shape uses an electrode probe which carries a plurality of sensing electrodes, each at known relative distances from the others. Then the known distances serve as a kind of ruler, allowing electrical measurements to be constrained in their relative spatial positions to occur at certain distances from one another, which are consistent with the distances between the sensing electrodes. Optionally, other constraints, are used as well; for example, a constraint that nearby points in the heart chamber should also be correspondingly nearby in their respective electrical field properties (e.g., but not only, lacking sharp discontinuities). The potential advantage of this method is that the electrical parameters being measured are not necessarily organized to a special arrangement of approximately linear crossing axes. This allows a wider range of electrical field configurations to be used, for example, configurations using transmitting electrodes positioned within the body space (optionally, electrodes of the mapping probe itself may be used as transmitting electrodes, albeit with some potential tradeoffs in utility, since the fields generated would then no longer be fixed). Intrabody transmitting electrodes in turn have potential advantages for removing sources of measurement variability such as the properties of extraneous tissue, and electrical contact of electrodes with skin; and for allowing an increased gradient of voltage with potentially increased signal to noise ratio.

The self-ruler method of measurement helps to constrain a measured map of surface position to something like its actual 3-D shape. It also becomes apparent from the position data that some regions have a different voltage gradient than others. That gradient difference can be affected by proximity of an esophagus. If the mapped distribution of gradients is relied on, the map may be used in comparisons as described for the first group of embodiments. Alternatively, the voltage gradient can be adjusted so that it matches some reference gradient in a region—but in order to accommodate this, the ruler length has to be adjusted accordingly. The distortion of the ruler distorts the mapped shape of the chamber. Additionally or alternatively, the ruler constraint is optionally not applied absolutely during reconstruction, but rather provided a weighting that allows the virtual ruler to shrink or expand slightly in order to improve, for example, a level of local electrical field self-correlation. In either instance, the error in the distorted shape can be used to estimate the position of the esophagus.

Another method of determining surface shape is to measure the magnitudes and directions of electrical field gradients in several different positions, and from this reconstruct an estimate of the overall shape of the heart chamber 404. For example, a simplifying assumption may be made that small gradient differences as a function of solid angle are due to differences in the distance in that direction of a substantially electrically uniform surrounding medium such as the cardiac wall. Blood vessels, being filled with relatively low-impedance blood, may be modeled to be "far away", for example (that is, located beyond open apertures), while expanses of heart chamber wall, with a higher impedance, are modeled to appear closer. However, the presence of the esophagus disturbs the simplifying assumption. A high impedance air pocket in an esophagus can make the heart chamber wall appear closer still, resulting in a bulge that may approximate a portion of a cylinder along the extent of the esophagus. Again, this type of error may be turned to advantage in estimating a position of the esophagus.

For any of the above-described methods of producing a measured map of a surface shape, similar methods of comparison to a reference map are available as were described for the first group of embodiments; but in the second group of embodiments using shapes of a surface in space as a basis of comparison. The reference map may be, for example, a map of a "true" shape of a heart chamber 404 (similar to a "non-esophagus" type reference map), or it may be a map that gives a shape distorted by a simulated and/or previously measured esophagus. It should also be noted that the partial cylinder shape also gives a method of finding and/or verifying an estimated esophagus position; for example, by matching a partial cylinder (or other suitable template shape, for example, a surface of a spheroid, ellipsoid, 3-D mesh, or other 3-D structure) to a bulge or indentation that comprises the deviation from the actual shape of the wall of the heart chamber 404.

It is noted that reference maps of surface shapes are optionally used as training tools for a physician, for example to train the physician to recognize esophagus shape on measured maps of surface shape.

According to some exemplary embodiments, the anatomical imaging component 416 comprises computer circuitry configured to analyze the received electric signals, for example, by combining the received signal with additional information, for example anatomical maps and/or imaging analysis results which are stored in memory 418. The result of the analysis, in some embodiments, is a measured map, which may be of the type that assigns electric field properties to positions, and/or of the type that explicitly determines an anatomical shape such as a lumen shape of a heart chamber, based on measured electric field properties. In some embodiments, the memory 418 stores programs and/or algorithms which can be used by control circuitry 414 to estimate the position of the esophagus, using the measured map and the reference maps(s). In some embodiments, memory 418 stores measured electric parameter values that were previously measured at different sites within a heart chamber (e.g., available for use by anatomical imaging component 416). In some embodiments, memory 418 comprises anatomical and/or electrical information of body tissues for example cardiac tissue and/or esophageal tissue.

According to some embodiments, control circuitry 414 estimates whether at least part of the esophagus 10 is present in an adverse location and/or whether the presence of the esophagus affects at least one outcome of a treatment. Alternatively or optionally, control circuitry 414 determines whether positioning at least one electrode at a specific target site for treating the cardiac tissue, for example by RF ablation will have an adverse effect on the esophageal tissue. In some embodiments, if application of treatment energy at the target site has no effect on the esophagus or that the effect on the esophagus is an allowed effect, then control circuitry 414 signals the field generator 412 to generate the treatment energy. Alternatively, if application of treatment energy at the target site is expected to have an adverse effect on the esophagus, then control circuitry 414 selects an alternative target site for the treatment, and/or modifies the treatment path and/or modifies at least one parameter of the treatment protocol. In some embodiments, the treatment protocol parameters comprise the intensity of the treatment energy and/or the duration of the treatment session and/or the interval between two consecutive treatment sessions. In some embodiments, the modified treatment protocol parameters allows for example, to avoid or to minimize the adverse effect of the treatment on the esophagus 10. In some embodiments, the treatment energy is delivered to the tissue by at least one electrode of electrodes 406.

According to some exemplary embodiments, if at least part of the Esophagus 10 is estimated to be present in an adverse location in relation to a selected treatment target site, then the control circuitry signals interface 420 to generate a human detectable indication, for example an alert signal, a light and/or a sound signal. Alternatively or additionally, the control circuitry 414 prevents the application of the treatment at the measured site. Optionally, control circuitry 414 selects an alternative target site for application of the treatment.

According to some exemplary embodiments, control circuitry 414 estimates the probability that application of treatment energy, for example RF energy at a selected treatment target site will cause esophagus injury, based on the estimated location of the esophagus, for example by simulating a treatment using the treatment parameters and the measured electric parameters of the tissue. In some embodiments, the simulation results are stored in memory 418. In some embodiments, device 400 comprises casing 422.

Exemplary Process for Estimating Esophagus Position Combined with a Treatment

Figure 4B:
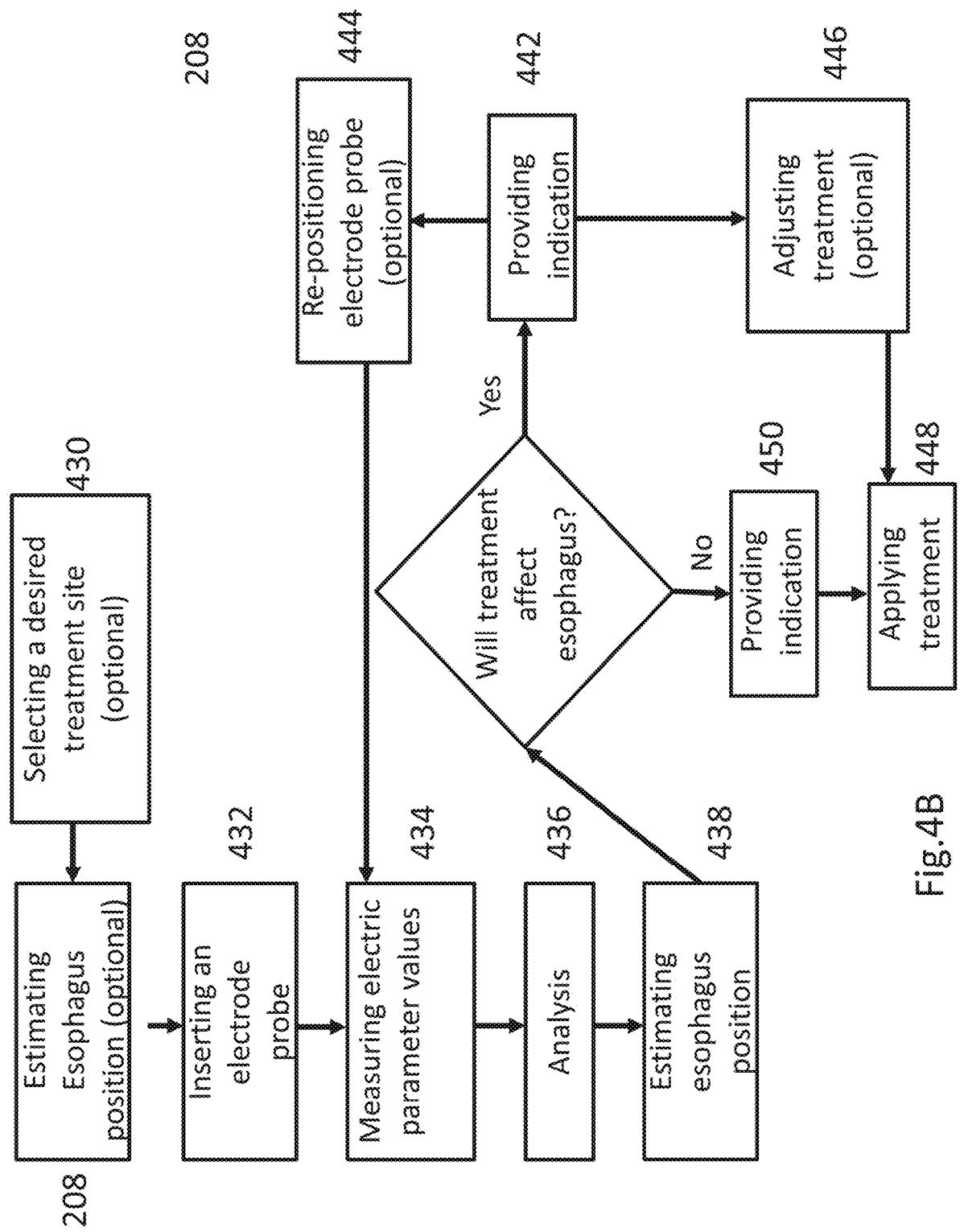
FIG. 4B is a flow chart of a process for estimating spatial relationship between the esophagus and the heart in combination with a treatment, according to some embodiments of the invention.

Reference is now made to FIG. 4B, depicting a flow chart for estimating the position of at least part of the esophagus prior to a treatment procedure, for example in order to avoid or to minimize the effect of the treatment on the esophagus, according to some embodiments of the invention.

According to some exemplary embodiments, a patient is diagnosed, for example a patient with atrial fibrillation, and a treatment procedure is selected. In some embodiments, the treatment procedure comprises ablating a selected region of the cardiac tissue. Optionally, a treatment site is selected at 430 based on at least one clinical parameter and/or based on the results of an imaging procedure, for example MRI, CT or ultrasound procedure. In some embodiments, the selected treatment procedure comprises RF ablation.

According to some exemplary embodiments, the position of the esophagus is estimated, as previously described at 208. In some embodiments, estimating the position of the esophagus allows for example, to select at least one target site or target region or a path for the treatment and/or to determine which regions of the cardiac tissue to avoid during the treatment in order to minimize an adverse effect of the tissue, for example esophagus injury.

According to some exemplary embodiments, an electrode probe, which includes at least one electrode, is inserted into a heart chamber, for example the LA at 432. In some embodiments the electrode probe is inserted, for example to measure at least one electric parameter, for example electric potential and/or impedance; and/or to apply the treatment energy, for example RF energy to the cardiac tissue. Optionally the electrode is placed at the treatment target site or at the treatment path that was previously selected at 430.

According to some exemplary embodiments, the electrode measures at least one electric parameter of the tissue at 434. In some embodiments, the electric parameter is measured (e.g., while moving the electrode and recording, for example, about 100 measurement recordings per second) at different locations within the LA and/or at the selected treatment target site or adjacent to the selected treatment target site. In some embodiments, the at least one electric parameter comprises electric potential and/or impedance.

In some embodiments, the electrode measures the electric parameter at 434 during application of an electric field to the tissue, for example by at least one additional electrode or at least one additional pair of electrodes, for example 2 pairs, 3 pairs, or 4 pairs. In some embodiments, the additional electrode or electrode pair is located on the electrode probe that was inserted into the heart chamber. Alternatively, the additional electrode or electrode pair is attached to the outer surface of the body, for example to the skin of the patient, optionally at selected locations on the skin.

According to some exemplary embodiments, the measured values of the electric parameter, for example electric potential, are analyzed at 436. In some embodiments, the analysis comprises generating an electric potential map or an impedance map based on the measured values of the electric parameter. In some embodiments, an additional parameter is used to help determine a measured map derived from the electric parameter: it may be a clinical parameter, for example an electrophysiological parameter. Alternatively or additionally, the additional parameter comprises an anatomical parameter of the tissue. Optionally, the additional parameter comprises the results of an imaging analysis procedure for example MRI, CT or ultrasound imaging analysis.

According to some exemplary embodiments, the analysis at 436 comprises comparing measured electric potential values with simulated values. The comparison may reveal differences which are due to disturbances in the electrical field due to the nearby presence of the esophagus.

In some embodiments, the comparison is of an electric potential map constructed based on measured values with a simulated electric potential map of the tissue. The simulated map may be understood as converting positions in a simulation into expected electric potentials or other electric field parameter values (without an esophagus), and the deviations are deviations from this. Additionally or alternatively, a simulation which includes simulation of an esophagus is considered to already include a deviation from the non-esophagus state, and to the extent that measured values match that simulation, the measured electric potential map shares the same deviation. Deviations in electric potential map may be understood to have a "shape", e.g., insofar as electrical potential magnitude varies to different values ("heights" or "distance", if was graphed) as a function of positions along an extent following the heart chamber wall.

Additionally or alternatively, in some embodiments, the measured map is a map of tissue positions (also referred to herein as a measured map of surface shape), wherein measured electrical potentials are used to determine positions of the tissue wall that comprise the map (a "wall shape"), without a prior assumption that there is a deviation of indicated tissue wall positions from actual wall positions due to the presence of an esophagus. Then the map being compared to is a map of actual heart chamber wall positions, and the deviation is described in terms of a deviation in physical shape.

In some embodiments (without prior assumption of esophagus effects, so that a true wall position measurement is what is "expected"), the electrical potential map may result in measurements which indicate an atrial wall which somewhat indents from its actual position. This may be due to effects within a region on local impedance measurements, that result from an inhomogeneity in dielectric properties that the esophageal tissue and/or air within the esophagus introduce to the region.

In some embodiments, the simulated electric potential map is generated as previously described at 209. Alternatively, the measured electric potential map is analyzed to identify specific regions which might indicate the presence of esophageal tissue proximal to the LA, for example by identifying shapes (e.g., plotting a magnitude as a function of position along the wall surface) substantially corresponding to a portion of a cylinder (e.g., an elliptical right cylinder) wherein the cylinder height extends generally along a rostro-caudal anatomical axis. In some embodiments, an axis of the cylinder cross-section extends substantially parallel to the LA wall having a length of about 5-15 mm, 10-20 mm, or another length. In some embodiments, deviations in measured "wall shape" from actual wall shape are distinguished by another pattern which superimposes on the position map of the LA wall.

In some embodiments, the measured electric potential map is compared to simulated electric potential maps which were generated based on estimated positions of the esophagus. In some embodiments, identifying a simulated map which is similar to the measured map allows for example, to estimate the position of the esophagus.

According to some exemplary embodiments, the position of at least part of the esophagus is estimated at 438, optionally based on the analysis of the measured electric parameter values as described at 436. In some embodiments, estimating the position of at least part of the esophagus comprises estimating a spatial relation between at least part of the esophagus and the LA or a treatment target site within the LA. Optionally, estimating the esophagus position comprises predicting whether application of treatment energy, for example RF energy at a selected target site within the LA will have an adverse effect on at least part of the esophagus.

According to some exemplary embodiments, if application of treatment energy at the selected treatment target site is predicted to have an adverse effect on the esophagus, for example to injure at least part of the esophageal tissue, then an indication, for example a human-detectable indication is delivered at 442. In some embodiments, the indication is delivered to a user of the device, for example a physician or a technician performing the procedure. Optionally, the indication comprises an alert signal. In some embodiments, the indication comprises information regarding an alternative treatment site, optionally based on the estimated esophagus position.

According to some exemplary embodiments, if application of treatment energy at a selected target site is predicted to have an adverse effect on the esophagus, then the electrode probe or at least one electrode of the electrode probe is re-positioned at 444. In some embodiments, the electrode is positioned at an alternative treatment site, optionally based on the estimated Esophagus position. In some embodiments, once the electrode is re-positioned, the electric parameter is measured at the new treatment target site, for example as described at 434.

According to some exemplary embodiments, if application of treatment energy at a selected target site is predicted to have an adverse effect on the esophagus, then at least one parameter of the treatment is modified or adjusted at 446, optionally based on the estimated esophagus position and/or based on a spatial relationship between the target site and the esophagus. In some embodiments, the at least one parameter comprises the duration of the treatment, the intensity of the treatment and/or an alternative treatment path, for example an alternative ablation path, which comprises at least one alternative treatment target site. Optionally, the at least one parameter comprises the number of treatment sessions, the duration of each treatment session or the interval between sequential treatment session.

According to some embodiments, once the at least one treatment parameter is modified or adjusted, a treatment is applied at 448. In some embodiments, the treatment is applied by at least one electrode or set of electrodes located on the electrode probe. Optionally, the treatment is applied by at least one electrode positioned inside the body or outside the body of the patient, for example by a skin electrode.

According to some exemplary embodiments, if application of treatment energy at a selected target site is not predicted to have an adverse effect on the esophagus, then an indication is provided to a user at 450. In some embodiments, the indication is delivered to a user of the device, for example a physician or a technician performing the procedure. In some embodiments, the delivered indication comprises a human detectable indication, for example a light or a sound indication. In some embodiments, a treatment is applied at 448, as previously described.

Exemplary Estimation of the Position of the Esophagus in Combination with an Ablation Process Reference is now made to FIG. 5 depicting a process for estimating the presence and/or position of at least part of the esophagus in combination with an ablation procedure, according to some embodiments of the invention.

According to some exemplary embodiments, the position of at least part of the esophagus is estimated at 501. In some embodiments, the esophagus position is estimated based on an imaging analysis, for example a CT, MRI or ultrasound imaging analysis. It should be noted that the esophagus is capable of moving relative to the heart (e.g., due to swallowing movements) over a period of time, so imaging-based estimation of esophagus position is preferably performed using an image taken very close in time to a treatment procedure that uses the position estimate.

In some embodiments, a map, for example an electric potential or an impedance map, is generated based on simulated electric potential or impedance values, and optionally based on the results of the imaging analysis. In some embodiments, the simulated map comprises electric potential or impedance values that are expected to be measured by an electrode placed within the heart cavity, for example the LA. In some embodiments, the estimated position of the esophagus at 501 comprises possible locations of the esophagus, optionally due to predicted movement of the esophagus, for example lateral movement of the esophagus relative to the heart. In some embodiments, each simulated map is generated based on a different estimated position of the esophagus, optionally in relationship to the heart. In some embodiments, at least one simulated map and/or the information regarding the estimated position of the esophagus are presented on a display, for example prior to or during the treatment.

According to some exemplary embodiments, at least one ablation treatment target site and/or an ablation path are planned at 502. In some embodiments, the ablation target site and/or the ablation path are selected based on at least one clinical parameter, for example an electrophysiological parameter. Additionally or optionally, the target site is selected based on anatomical information, for example an anatomical map and/or based on the results of at least one imaging analysis, for example CT, MRI or ultrasound analysis. In some embodiments, the ablation target site and/or the ablation path are selected based on at least one simulated map, for example at least one simulated map that was generated at 501.

According to some exemplary embodiments, at least one electrode is positioned within a heart chamber and/or at the planned treatment target site or treatment path, for example the planned target site or path, at 504. In some embodiments, the target site or path is located at the LA, for example at the cardiac tissue of the LA. In some embodiments, the electrode is positioned based on the simulated map.

According to some exemplary embodiments, the electrode measures at least one electric parameter, for example electric potential within the LA, optionally at the target site or adjacent to the target site at 506, and/or at a multiplicity of other sites. In some embodiments, the electric parameter is measured during application of an electric field to the body, optionally to the skin. In some embodiments, the simulated map is modified based on the measured electric parameter values that are measured from within the LA. Alternatively, the measured electric parameter values are compared to simulated values. In some embodiments, the measured electric parameter values are used to generate an electric potential map or and impedance map.

According to some exemplary embodiments, the position of the esophagus or a spatial relationship between the LA and at least part of the esophagus is estimated at 508. Optionally, esophageal tissue proximity to a selected target site or to the selected treatment path is estimated.

According to some exemplary embodiments, the position of the esophagus is estimated by identifying, in the maps regions that exhibit deviations in the measured electric parameter values compared to estimated values, which are related to the effect of a proximal esophageal tissue on the measured values. In some embodiments, the estimated values are based on multiple electric parameter measurements in many subjects. Alternatively, the esophagus position is estimated by comparing the map based on the measured values to the simulated maps, to identify the simulated map that is most similar to the map of measured values. In some embodiments, the esophagus position is estimated by comparing the measured values to simulated values that reflect different predicted positions of the esophagus. In some embodiments, if patient is awake and cooperative, swallowing manipulation can allow an expert performing the procedure to detect esophagus and assist in verification electrical mapping diagnostic.

In some embodiments, the measured electric parameter values, for example electric potential values are used to indicate a spatial relationship, for example distance between the measurement site and/or the electrode probe and esophageal tissue. In some embodiments, the measured electric parameter values are used to estimate a spatial relationship, for example distance between an ablation target site and/or an ablation path to esophageal tissue, without the need to generate a map based on these measured values. In some embodiments, the measured electric parameter values are used to determine whether the estimated spatial relationship is a targeted or an allowed spatial relationship before the ablation. In some embodiments, a targeted or an allowed spatial relationship comprises a spatial relationship between at least part of the esophagus and a selected ablation target site that allows, for example to deliver RF energy to the tissue at the target site without affecting the at least part of the esophagus, or that the effect on the esophagus is an allowed effect, for example an effect that does not lead to esophagus injury. Optionally, a targeted spatial relationship comprises that the esophagus is not detected at the measurement site of the electric parameter values.

According to some exemplary embodiments, if ablating the target site or along the target path is predicted to have no adverse effects on the esophagus or that the effect on the esophagus is predicted to be an allowed effect, then an ablation procedure is initiated at 516. Optionally, the ablation procedure is initiated if the ablation target site is in a targeted or an allowed spatial relation, for example a targeted or an allowed distance from the esophagus, based on the measured electric parameter values. In some embodiments, if ablation at the target site or along the target path is allowed, then an indication is provided.

According to some exemplary embodiments, if ablating the target site or along the target path is predicted to have adverse effect on the esophagus, for example to injure the esophagus, based on the measured electric parameter values, then an indication is provided. Additionally, alternative ablation sites and/or an alternative ablation path are selected at 510. Alternatively, at least one parameter of the ablation treatment is modified, for example to minimize or to avoid the adverse effect, at 512. In some embodiments, the modified ablation parameter is automatically selected from a list comprising the intensity of the ablation, the duration of each ablation pulse, the ablation frequency, and/or the time interval between at least two consecutive ablation sessions.

According to some exemplary embodiments, if ablating the target site or along the target path is predicted to have adverse effect on the esophagus, then the esophagus is moved to a targeted location at 513. Optionally, movement of the esophagus is accomplished by encouraging the subject (if conscious) to swallow; this can result in esophagus movement away from the target site. The movement can be monitored and verified as for the original estimate of esophagus position. In some embodiments, the esophagus is moved, for example by insertion of a device into the esophagus that allows to safely move the esophagus and optionally to fix the esophagus at a targeted position.

According to some exemplary embodiments, if the electrode is placed at an alternative target site for ablation, the verification is performed at 514. In some embodiments, verification comprises measuring at least one electric parameter at the alternative target site, and estimating a spatial relationship between the alternative target site and at least part of the esophagus, before ablating.

According to some exemplary embodiments, an ablation procedure is applied at 516. In some embodiments, during the ablation procedure an electric potential map or a map which is based on measured and/or simulated electric potential values is displayed. In some embodiments, the displayed map is used to position the ablation probe within the heart chamber at locations that are in an allowed spatial relationship, for example distance from at least part of the esophagus.

According to some exemplary embodiments, after each ablation session, additional measurements of the electric potential are performed. In some embodiments, the additional measurements are used to update an existing electric potential or impedance map, optionally to identify movements of the esophagus during or after the ablation session.

Exemplary Process for Simulating an Electric Potential or Impedance Map

Reference is now made to FIG. 6A depicting a process for generating an electric potential or impedance map, according to some embodiments of the invention.

According to some exemplary embodiments, an imaging analysis is performed at 602, for example to estimate the position of the esophagus, the heart and other tissues or organs. In some embodiments, the imaging analysis comprises CT, MRI or ultrasound imaging analysis.

According to some exemplary embodiments, a simulation of electric parameter values is performed at 604. In some embodiments, electric potential and/or impedance values are simulated as they would be measured by at least one electrode from within the heart chamber, for example the LA. In some embodiments, the simulation is based on the position and the number of the electrodes that will be used to generate the electric field, the electric field frequency that will be applied to the body by each electrode or pair of electrodes, and on the tissue types surrounding the LA and their respective dielectric properties.

According to some exemplary embodiments, based on the simulated values, a simulated map is generated at 606, for example a simulated electric potential or impedance map. Optionally, the map is generated by combining the simulated electric parameters values with anatomical data, for example anatomical data that was obtained in imaging analysis 602.

According to some exemplary embodiments, at least one electrode is inserted into a heart chamber or into a blood vessel to measure at least one electric parameter of the tissue from at least one and preferably from a multiplicity of locations, for example at 610. Optionally, impedance values are calculated from the measured electric potential values. In some embodiments, the electric potential or impedance values are used to generate a map, for example an electric potential or an impedance map.

In some embodiments, the measured electric potential or impedance values are used to update the simulated map at 612. Alternatively the generated electric potential or impedance map is used to update the simulated map. In some embodiments, the updated map which describes the updated position of the esophagus and/or the proximity of esophageal tissue to the LA is displayed to an expert before and/or during and/or after a treatment, for example an RF ablation treatment. In some embodiments, the updated map allows the expert for example, to place the ablation electrode at a location or to plan an ablation path that will not result with esophagus injury once the treatment energy is applied.

Exemplary Simulated Maps

According to some exemplary embodiments, simulation results are obtained by modeling electric field propagation in an area modeled to contain material having the dielectric properties associated with the tissues imaged in the CT scan (or other anatomical data). In some embodiments, tissue type identity is assigned based on automatic segmentation of the CT scan imaging results. It is a potential advantage to use a high-resolution scan. Example of high resolution scan is a CT scan with slices of between 1 mm-3 mm. Higher resolution, should it be available, is preferable. In some embodiments, the scan is optionally used as a basis of the segmentation, as this sets the conditions of the field simulation more nearly to the actual situation. In some embodiments, post-processing, optionally manually guided, is performed to remove segmentation artifacts.

Optionally, post-processing, e.g., for cleaning up segmentation, uses capabilities of commercially available imaging system, such as a Carto™ or Insight™ system. In some embodiments, post-processing is performed under the guidance of an imaging technician experienced in tasks of anatomical segmentation. In general, results of the electromagnetic simulation are dependent on the degree of care devoted to obtaining accurate, high-resolution anatomical data. The higher resolution of the scanned tissues should also be preserved in the simulation modeling itself.

Reference is now made to FIGS. 7A-7I depicting simulated electric potential maps of the LA, according to some exemplary embodiments of the invention.

According to some exemplary embodiments, simulated electric potential maps are generated by simulation of electric potential values as if they are measured from within at least part of the heart, for example from within the LA. In some embodiments, the simulation is based on the dielectric properties of cardiac tissues and other tissue types surrounding the LA. In addition, simulation of LA electric potential values is based on a simulated position of an electrode probe within the LA, position of electrodes on the skin for application of electric fields, and on other parameters of the applied electric fields for example frequencies and intensity. In some embodiments, each of the simulated maps is generated based on a different estimated position of the esophagus, and represents the effect of the esophagus at this estimated position on the simulated electric potential values. Alternatively, the simulated maps are prepared based on a different spatial relationship between a simulated measurement site and at least part of the esophagus.

Figures 7C, 7D, 7E, 7F:
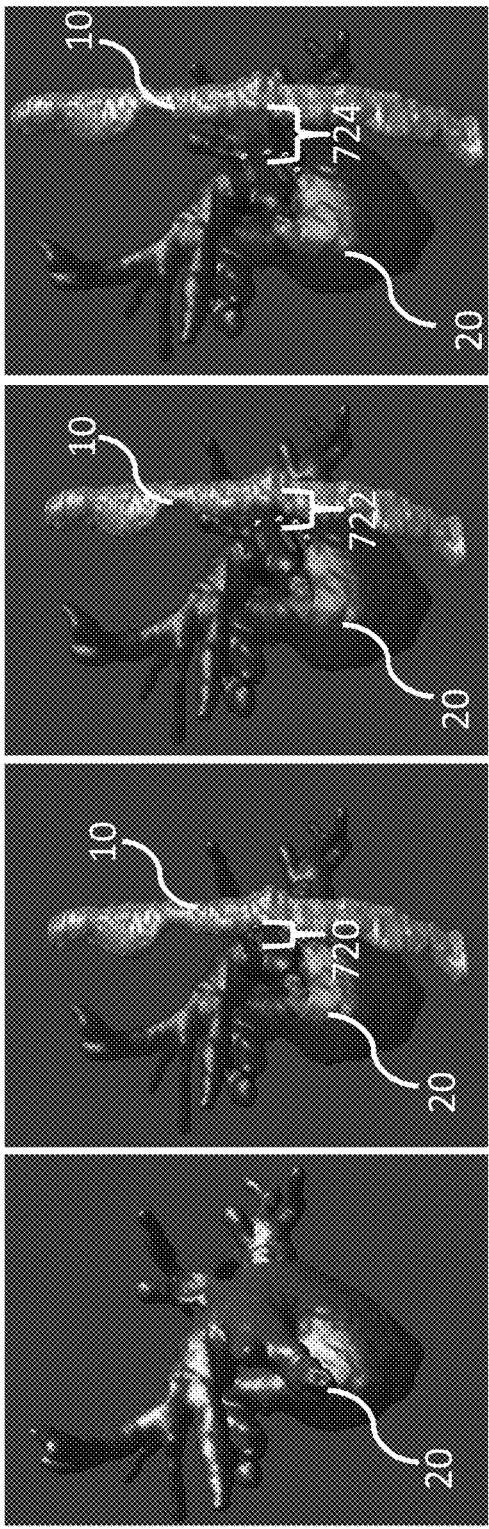
Figure 7G:
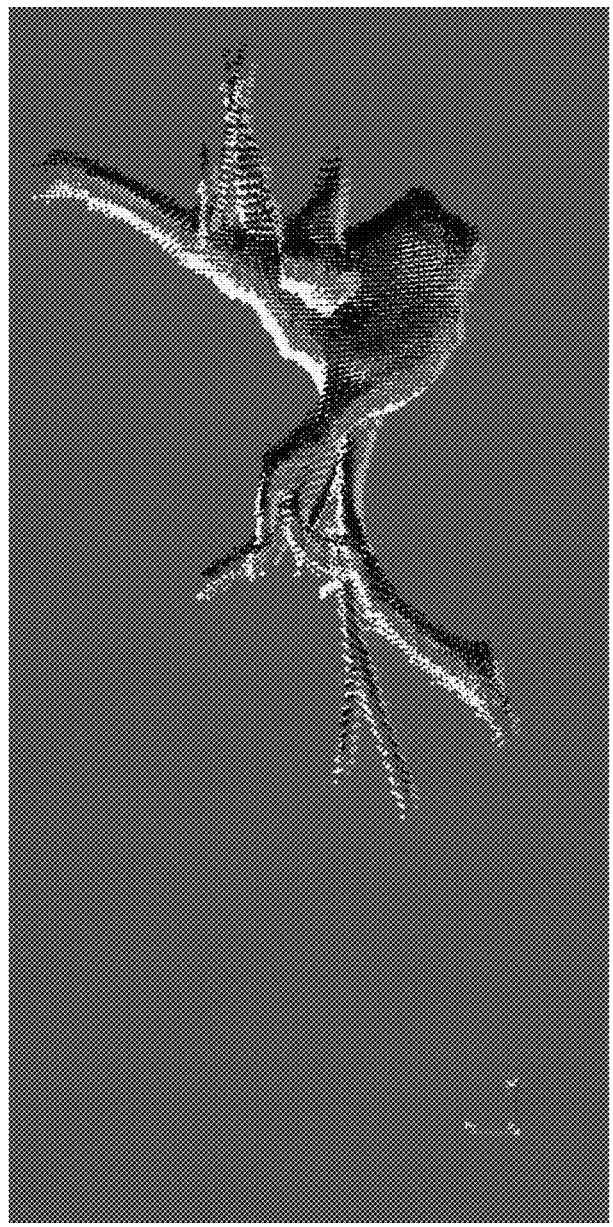

According to some exemplary embodiments, for example as shown in FIGS. 7A and 7B the white electric potential simulated map shown in FIG. 7B is a simulated electric potential map that was generated based on an assumption that the esophagus is not affecting the electric field inside the heart 20. In some embodiments, for example as shown in FIGS. 7D-7F, the simulated electric potential maps are generated based on the assumption that the esophagus 10 is positioned at different spatial relationships, for example in a different distance, from the heart 20. In some embodiments, based on the different positions of the esophagus different simulated electric potential maps are generated. In some embodiments, for example as shown in FIG. 7G each colored simulated map reflects a different spatial relationship between the esophagus and the heart. For example, the red simulation map is generated based on the assumption that the esophagus 10 is positioned in distance 720 from the heart 20. Additionally, the green and the black colored simulation maps are generated based on the assumption that the esophagus 10 is positioned in distances 722 and 724, respectively. In some embodiments, a minimal spatial difference of 2% between the white, red, green and black colored electric potential maps shown for example in FIG. 7G, allows to identify possible positions of the esophagus.

According to some exemplary embodiments, the position of the LA is determined based for example, on CT scanning results and different simulated electric potential maps are generated based on the assumption that the esophagus is placed in different distances from the LA, as shown for example in FIGS. 7H and 7I. In some embodiments, FIG. 7I is an overlay of simulated maps that were prepared based on estimated positions of the esophagus related to LA 30, shown in FIG. 7H.

Exemplary Simulated Maps

Reference is now made to FIGS. 8A-8E, which schematically represent views of a phantom left atrium within which electrode probe voltage mapping measurements have been performed with and without an adjacent air-filled tube simulating an esophagus, according to some embodiments of the present disclosure.

Figure 8A:
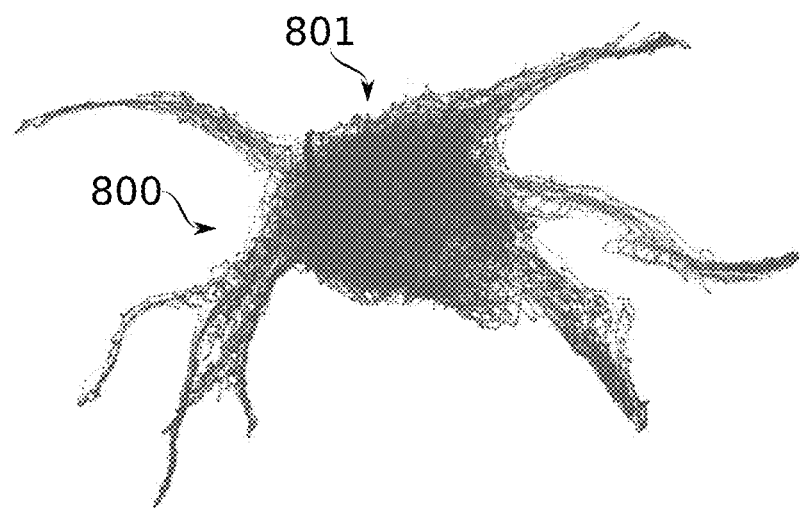
FIGS. 8A-8E, schematically represent views of a phantom left atrium within which electrode probe voltage mapping measurements have been performed with and without an adjacent air-filled tube simulating an esophagus, according to some embodiments of the present disclosure.
Figure 8B:
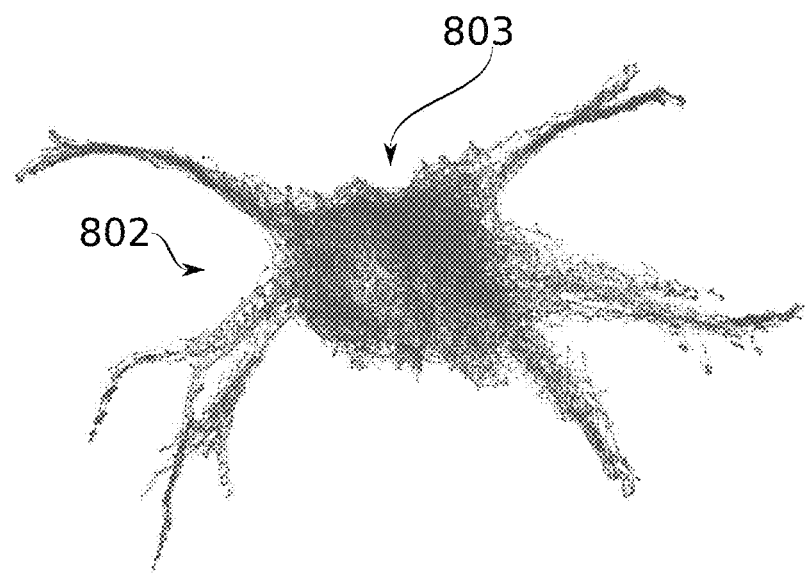
Figure 8C:
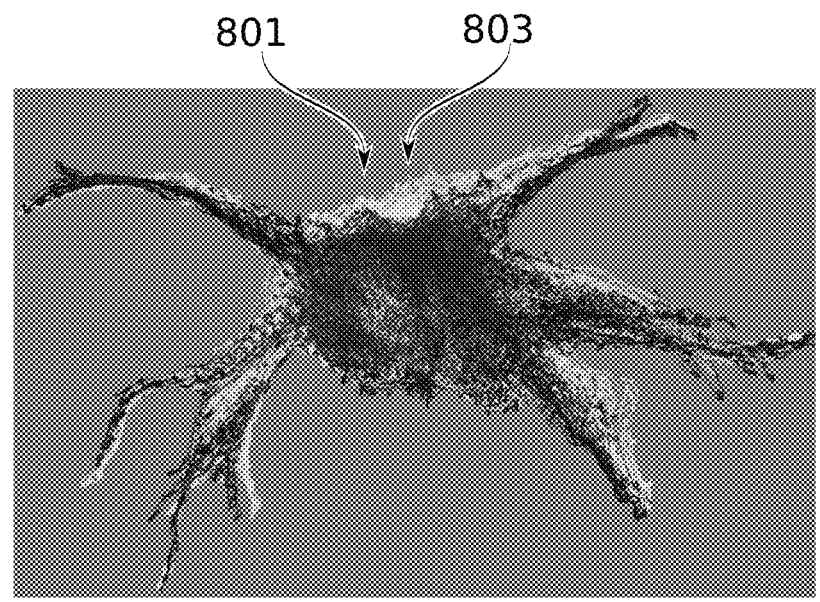

FIGS. 8A and 8B each show a point cloud of voltage measurements, wherein the measurement position has been determined using an electrode probe which carries a plurality of sensing electrodes, each at known relative positions (at least known distance) with respect to one another. The known relative positions were used as a constraint in finding the positions of the measurement points with respect to one another. In some embodiments, the constraint may be soft, that is, a mapping that keeps the distance between the electrodes equal to the distance in reality is preferred over a mapping that does not keep these distances equal, but the latter is not absolutely prevented. During the measurements of FIG. 8B, but not FIG. 8A, a tube filled with air was submerged adjacent to the phantom at position 803. The resulting indentation (deviation) at 803 of FIG. 8B can be observed relative to the shape of region 801 in FIG. 8A. FIG. 8C is a differential image, with the point cloud of FIG. 8B dark and the point cloud of FIG. 8A light. The difference between the two point clouds is seen as the lighter points of region 801 showing through the gap left in region 803.

Figure 8D:
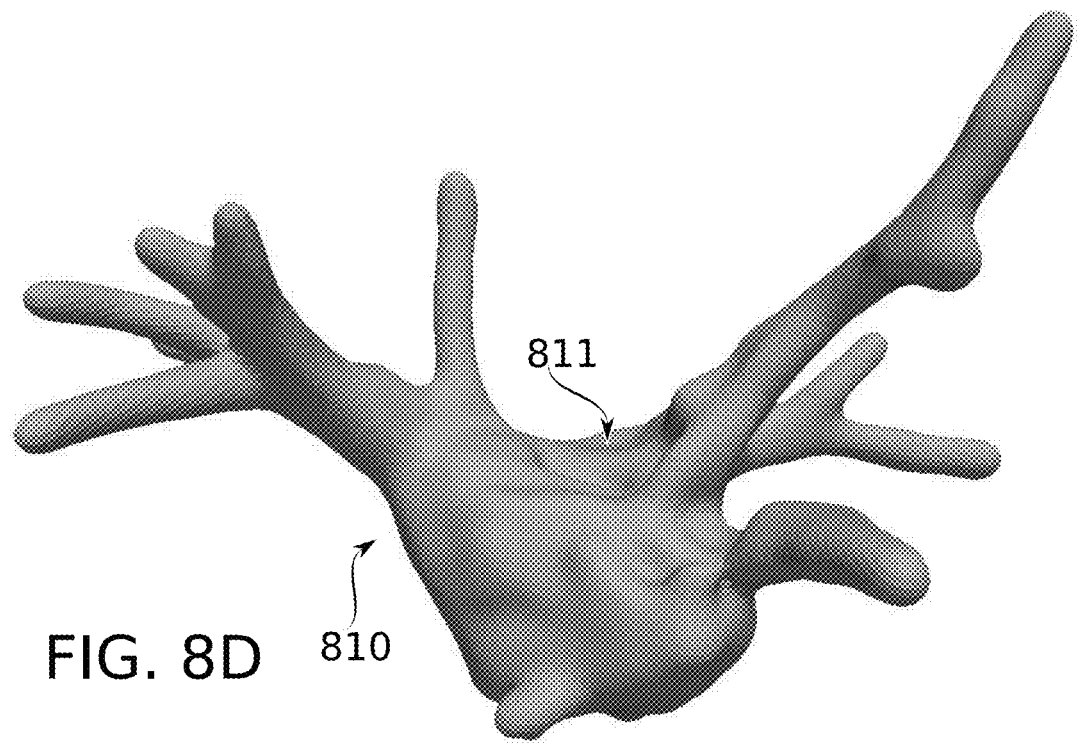
Figure 8E:
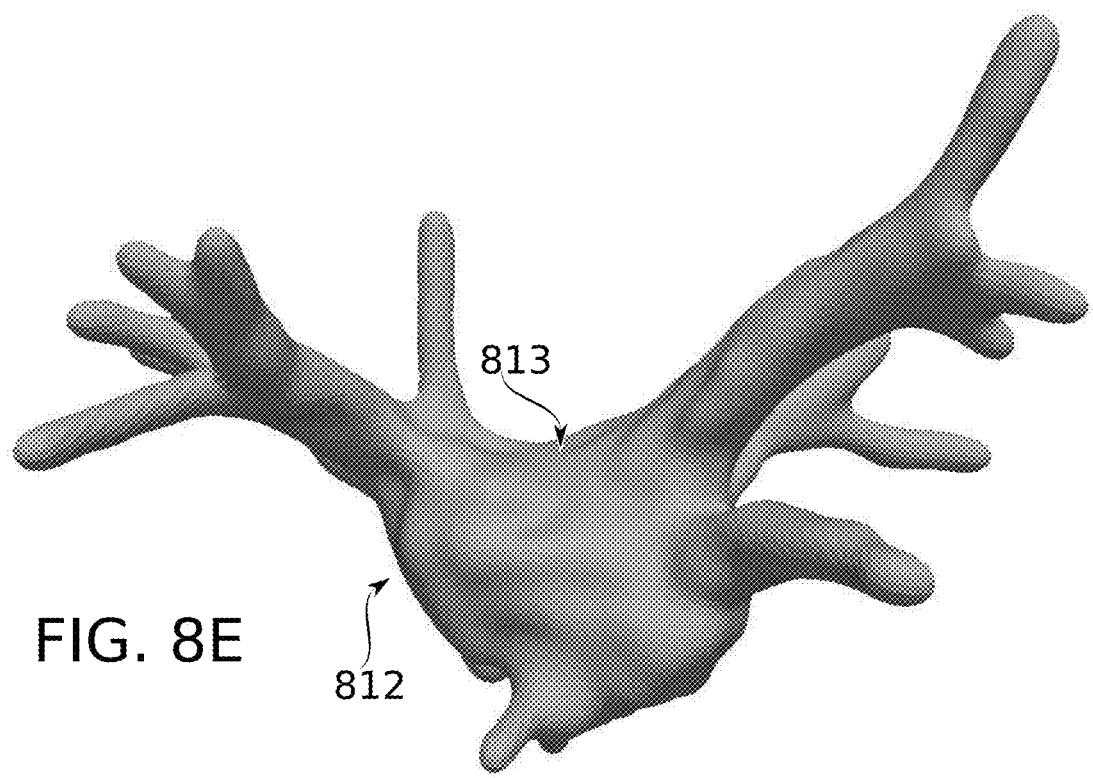

FIGS. 8D and 8E represent rolling marble reconstructions 810, 812 based on point clouds acquired as described for FIGS. 8A and 8B, respectively. Rolling marble reconstruction rolls a virtual sphere of a certain diameter over the body of a point cloud with a controlled degree of intrusion, defining a surface that contains the measurements of the point cloud within it. In FIG. 8E, a deviation (indentation) at 813 appears due to the influence of the air-filled tube, which is absent at 811.

General

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of estimating a spatial relationship between at least a part of a patient esophagus and a heart chamber, comprising:
    measuring at least one electric parameter at one or more positions within said heart chamber to obtain measured values, using an electrode placed at said one or more positions, wherein said electric parameter is of electric fields generated from electrodes positioned outside said esophagus;
    wherein the electric field-generating electrodes positioned outside the esophagus comprise at least 3 pairs of electrodes placed on the skin of said patient and applying at least 3 electric fields to said heart chamber, and used for determining a position of the electrode within the heart chamber;
    determining a position of the electrode within the heart chamber, using the measured values; and
    estimating said spatial relationship between at least a part of a patient esophagus and a heart chamber based on said measured values and the determined position.

2. The method of claim 1, wherein said estimating comprises estimating said spatial relationship between a treatment target site in said heart chamber and the esophagus.

3. The method of claim 1, further comprising:
    generating an electric property map based on the measured values.

4. The method of claim 1, further comprising:
    generating an anatomical map of the heart chamber or a portion thereof based on the measured values.

5. The method of claim 3, wherein said estimating further comprises identifying at least one region within said electric property map having deviations in said measured values resulted from the proximity of said esophagus to said heart chamber.

6. The method of claim 5, wherein the deviations are deviations of the electric property map from map values corresponding to the absence of an esophagus in proximity to the at least one region.

7. The method of claim 5, wherein the deviations are deviations of the electric property map toward map values corresponding to the presence of an esophagus in proximity to the at least one region.

8. The method of claim 1, further comprising:
    determining whether said spatial relationship is a targeted spatial relationship.

9. The method of claim 8, further comprising:
    indicating if said spatial relationship is not a targeted spatial relationship.

10. The method of claim 8, further comprising:
    automatically suggesting an alternative target site if said spatial relationship is not a targeted relationship.

11. The method of claim 1, wherein said electrode positioned within said heart chamber is used both to estimate the position of the esophagus and for ablation.

12. The method of claim 2, wherein said estimating comprises estimating that said esophagus is not within a certain range from the treatment target site.

13. The method of claim 2, wherein said treatment target site comprises an ablation target site.

14. The method of claim 1, comprising estimating an effect of a treatment in the heart chamber on said esophagus based on said spatial relationship.

15. A method for estimating from within a heart chamber a probability to affect at least part of the esophagus by treating said heart chamber, comprising:
measuring at least one electric parameter using a measurement electrode positioned within said heart chamber, wherein said electric parameter is of an electric field generated from electrodes positioned outside said esophagus;
wherein the electric field-generating electrodes positioned outside the esophagus comprise at least 3 pairs of electrodes placed on the skin of said patient and applying at least 3 electric fields to said heart chamber, and used for determining a position of the electrode within the heart chamber; and
estimating the probability to affect said at least part of the esophagus based on measured values of said electric parameter.

16. The method of claim 15, further comprising:
generating an electric property map based on measured values of said electric parameter, after said measuring;
wherein said estimating further comprises identifying at least one region within said map having variations in said measured values resulted from the proximity of said esophagus to said heart chamber.

17. The method of claim 15, further comprising:
generating an electric potential map based on measured values of said electric parameter, after said measuring;
comparing said electric potential map to at least one simulated electric potential map;
identifying at least one region within said electric potential map generated based on the measured values, said at least one region having variations resulted from a proximity of said esophagus to said heart chamber, based on said comparing;
wherein said estimating is based on said variations.

18. The method of claim 15, further comprising:
generating an electric potential map based on measured values of said electric parameter, after said measuring;
comparing said electric potential map to one or more simulated electric potential maps;
identifying one or more similar maps of said simulated electric potential maps similar to said electric potential map generated based on measured values;
wherein said estimating is based on the at least one simulated electric potential map identified.

19. A device for estimating esophagus position, comprising:
A field generator configured to generate electric fields in the esophagus via electrodes outside the esophagus;
wherein the electric field-generating electrodes positioned outside the esophagus comprise at least 3 pairs of electrodes configured to be placed on the skin of said patient, and the field generator is configured to apply at least 3 electric fields to said heart chamber and esophagus using the at least 3 pairs of electrodes;
measuring circuitry configured to receive signal measurements of an electric parameter of the electric field generated by said field generator, wherein the measuring circuitry is configured to measure from an electrode probe navigating within a heart chamber;
control circuitry, configured to model the heart chamber based on the signal measurements, and positions of the electrode probe calculated therefrom, and to estimate a position of at least part of an esophagus adjacent to the heart chamber, based on said signal measurements and said positions.

20. The device of claim 19, further comprising:
a digital computer memory;
wherein said control circuitry estimates said esophagus position by comparing a measured map constructed to associate the signal measurements with positions in the heart chamber to one or more reference maps, stored in said digital computer memory, wherein the reference maps associate predicted values of said electric parameter with the positions in the heart chamber.

21. The device of claim 20, wherein at least one of the reference maps is a simulated map.

22. The device of claim 20, wherein at least one of the reference maps is a map constructed using a measured map having a known position of the at least part of the esophagus adjacent to the heart chamber.

23. The device of claim 19, wherein the control circuitry estimates the esophagus position using a template shape to match a shape of the measured map of the heart chamber.

24. The device of claim 19, wherein said measuring circuitry is connected to a catheter system configured to be at least partly placed within a heart chamber to measure said electric parameter.

25. The device of claim 19, further comprising:
at least one electrode connectable to said measuring circuitry; wherein said electrode is shaped and sized to be placed within a heart chamber to measure said electric parameter.

26. The device of claim 19, comprising:
a field generator; wherein said field generator is configured to deliver an energy field to a heart chamber through an electrode placed in said heart chamber based on said esophagus position of said at least part of the esophagus.

* * * * *